United States Patent [19]

Narisada et al.

[11] Patent Number: 4,592,865
[45] Date of Patent: Jun. 3, 1986

[54] AZETIDINONE INTERMEDIATES FOR CEPHALOSPORIN ANALOGS

[75] Inventors: Masayuki Narisada; Hiroshi Onoue; Teruji Tsuji; Yasuhiro Nishitani; Mitsuru Yoshioka, all of Osaka; Yoshio Hamashima, Kyoto; Wataru Nagata, Hyogo, all of Japan

[73] Assignee: Shionogi & Co., Ltd., Osaka, Japan

[21] Appl. No.: 589,670

[22] Filed: Mar. 13, 1984

Related U.S. Application Data

[60] Division of Ser. No. 322,663, Nov. 18, 1981, abandoned, which is a continuation of Ser. No. 134,134, Mar. 26, 1980, abandoned, which is a continuation-in-part of Ser. No. 28,323, Apr. 9, 1979, abandoned, which is a continuation of Ser. No. 823,175, Aug. 8, 1977, abandoned.

[30] Foreign Application Priority Data

Aug. 9, 1976 [GB] United Kingdom ............... 33109/76
Jun. 30, 1977 [GB] United Kingdom ............... 27511/77

[51] Int. Cl.[4] ................. C07D 205/08; C07D 405/12; C07D 498/04; C07D 403/12

[52] U.S. Cl. ............................ 260/239 A; 260/245.4; 260/330.3; 260/330.9; 544/90; 544/359; 544/366; 544/367; 544/182; 544/214; 544/215; 544/219

[58] Field of Search ............ 260/239 A, 330.3, 330.9, 260/245.4; 544/359, 366, 367

[56] References Cited

U.S. PATENT DOCUMENTS

| | | | |
|---|---|---|---|
| 3,896,119 | 7/1975 | Klinger | 424/250 |
| 4,115,984 | 7/1979 | Yoshioka et al. | 260/239 A |
| 4,143,038 | 3/1979 | Narisada et al. | 260/239 A |

OTHER PUBLICATIONS

Stoodley et al., J. Chem. Soc., 1973, 2105.
Colombeau et al., Chem. Abs. 72, 132996a (1970).
Moppett et al., Chem. Abs. 70, 28353M (1969).
Fieser & Fieser, "Reagents for Organic Synthesis", vol. 1, pp. 1276-1284.
Yamamoto et al., Heterocycles, 8, 283 (1977).
Ferles et al., Chem. Abs. 85, 62924t (1976).
Perrone et al., J. Chem. Soc., Chem. Comm., 1982 pp. 933-935.
Aratani et al., J. Org. Chem., 1980, 45, pp. 3682-3686.
Nausada et al., I Chem. Abs. 88, 190579h (1978).
Nausada et al. II, Chem. Abs. 88, 170055f (1977).

*Primary Examiner*—Mark L. Berch
*Attorney, Agent, or Firm*—Wenderoth, Lind & Ponack

[57] ABSTRACT

Intermediates of the following formula are useful for the synthesis of 1-oxacephalosporins. Their preparation from penicillins and the transformation process to make 1-oxacephalosporins are disclosed. The compounds are of the formula:

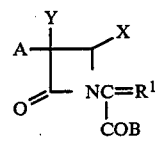

wherein
A is amino or a selected acylamino;
COB is carboxy or a selected protected-carboxy;
X is halogen or the group OR
in which R is a group represented by following formulas:

—CH$_2$C≡CH, —CH$_2$C≡CNu, —CH$_2$CH=CH$_2$,

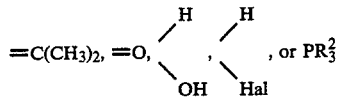

—CH$_2$CH—CH$_2$, —CH$_2$CHCH$_2$Nu or —CH$_2$COCH$_2$Nu
　　　＼／　　　　　　｜
　　　　O　　　　　　OH wherein Nu is a selected nucleophilic group;
R[1] is a group of the following formula:

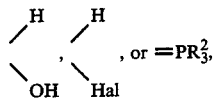

in which Hal is halogen or alkylsulfonyloxy and
R[2] is alkyl or aryl; and
Y is hydrogen or methoxy; with the proviso that when R is propargyl or 2-oxopropyl and
R[1] is $$\diagup^H, \diagup^H, \text{ or } =PR_3^2,$$
　＼OH　＼Hal A is in the 3α-configuration and Y is 3β-hydrogen or
A is in the 3β-configuration and Y is 3α-methoxy.

7 Claims, No Drawings

AZETIDINONE INTERMEDIATES FOR CEPHALOSPORIN ANALOGS

This application is a division of application Ser. No. 322,663, filed Nov. 18, 1981 (now abandoned) which application is in turn a continuation of application Ser. No. 134,134 filed Mar. 16, 1980 (now abandoned), which is a continuation-in-part of application Ser. No. 028,323, filed Apr. 9, 1979 (now abandoned) which is in turn a continuation of application Ser. No. 823,175 filed Aug. 8, 1977 (now abandoned).

This invention relates to intermediates for the synthesis of cephalosporin analogs from penicillins, which intermediates are represented by the following formula (I):

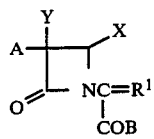

wherein
A is amino or acylamino selected from
(1) phenylacetamido,
(2) phenoxyacetamido,
(3) benzamido optionally substituted by a ($C_1$ to $C_3$) alkyl, nitro, cyano or a halogen,
(4) thienylacetamido,
(5) α-hydroxy- or ($C_1$ to $C_5$)alkanoyloxy-α-phenylacetamido,
(6) N—($C_1$ to $C_5$)alkoxycarbonyl-α-(phenyl or p-hydroxyphenyl)glycinamido,
(7) α-(phenyl or p-hydroxyphenyl)malonamido the carboxy group of which is optionally esterified with ($C_1$ to $C_5$)-alkyl, ($C_7$ to $C_{13}$)aralkyl or ($C_6$ to $C_9$)aryl, and the p-hydroxy group of which is optionally protected with ($C_1$ to $C_5$)alkyl, ($C_7$ to $C_{13}$) aralkyl or ($C_1$ to $C_5$)alkanoyl,
(8) thienylmalonamido the carboxy group of which is optionally esterified with ($C_1$ to $C_5$)alkyl, ($C_7$ to $C_{13}$)aralkyl or ($C_6$ to $C_9$)aryl,
(9) N-(4—($C_1$ to $C_3$)alkyl-2,3-dioxopiperazin-1-yl) carbonyl-α-phenylglycinamido,
(10) ($C_1$ to $C_5$)alkoxycarbonyl amino,
(11) ($C_5$ to $C_7$)cycloalkoxycarbonyl amino,
(12) ($C_4$ to $C_8$) cycloalkyl alkoxycarbonyl amino, and
(13) ($C_1$ to $C_5$)alkanesulfonyl($C_2$ to $C_5$)alkoxycarbonyl amino;
COB is carboxy or protected carboxy selected from those forming
($C_1$ to $C_5$)alkyl esters,
($C_2$ to $C_{10}$)alkanoylalkyl esters,
($C_1$ to $C_5$)haloalkyl esters,
($C_2$ to $C_{10}$)alkoxyalkyl esters,
($C_1$ to $C_{10}$)aminoalkyl esters,
monocyclic aryl ester,
mono- or bi-cyclic aralkyl esters, esters with a ($C_1$ to $C_{10}$)oxim,
esters with ($C_1$ to $C_5$)-N-alkoxyamides,
N,N'-diisobutylhydrazide,
alkali metal salts,
alkaline earth metal salts, and
($C_1$ to $C_6$)alkylamine salts;
X is halogen or the group β-OR
in which R is a group represented by the formula

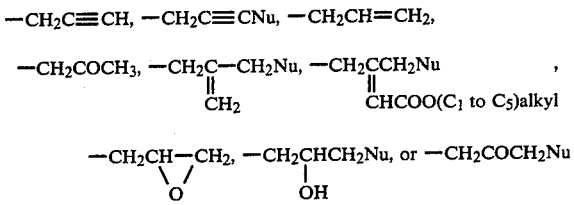

where Nu is a nucleophilic group selected from hydroxy, ($C_1$ to $C_5$)alkoxy, ($C_1$ to $C_5$)alkylthio, ($C_1$ to $C_5$)alkanoyloxy, ($C_1$ to $C_5$)alkanoylthio, monocyclic arylthio, monocyclic aralkylthio, tetrazolylthio, ($C_1$ to $C_5$)alkyltetrazolylthio, ($C_1$ to $C_5$)alkoxycarbonylmethyltetrazolylthio, thiadiazolylthio, ($C_1$ to $C_5$)alkylthiadiazolylthio, carboxymethylthiadiazolylthio, triazolylthio, ($C_1$ to $C_5$)alkyldihydrotriazinylthio, and chloro;
$R^1$ is a group of the formula:

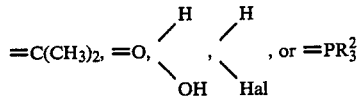

in which Hal is halogen or ($C_1$ to $C_6$)alkylsulfonyloxy, and $R^2$ is ($C_1$ to $C_5$)alkyl or monocyclic aryl; and
Y is hydrogen or methoxy; with the proviso that when R is propargyl or —CH$_2$COCH$_3$ and $R^1$ is

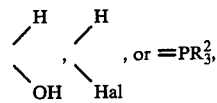

A is in the 3α-configuration and Y is 3β-hydrogen or
A is in the 3β-configuration and Y is 3α-methoxy.
In a particular aspect of this invention compounds of the above formula (I) are provided in which when X is OR it is in the β-configuration and when Y is hydrogen, A is in the α-configuration and when Y is methoxy, A is in the β-configuration. These compounds are especially suitable as intermediates in the preparation of 7-methoxy-1-oxacephalosporins.

The said groups A, COB and Nu are those conventional in the chemistry of penicillins and cephalosporins.
In the above definitions,
the ($C_1$ to $C_5$)alkanoyl part in alkanoyl, alkanoyloxy, alkanoylthio, etc. includes formyl, acetyl, propionyl, butyryl, isobutyryl, valeryl, isovaleryl and pivaloyl;
the ($C_1$ to $C_5$)alkyl part in alkyl, alkoxy, alkoxycarbonyl, alkylthio, etc. includes methyl, ethyl, propyl, isopropyl, butyl, isobutyl, t-butyl, pentyl and isopentyl;
the ($C_7$ to $C_{13}$)aralkyl part in aralkyl, aralkoxy, aralkoxycarbonyl, etc. includes benzyl, tolylmethyl, xylylmethyl, methoxybenzyl, ethoxybenzyl, halobenzyl, nitrobenzyl and diphenylmethyl;
the ($C_6$ to $C_9$)aryl part in aryl, aryloxy etc. includes phenyl, tolyl, xylyl and indanyl;
the ($C_5$ to $C_7$)cycloalkoxy includes cyclopentyloxy, cyclohexyloxy, and cycloheptyloxy;
the ($C_4$ to $C_8$)cycloalkyl alkoxy includes cyclopropylmethoxy, cyclopropylethoxy, cyclopentylethoxy, cyclohexylmethoxy and cyclohexylethoxy;

the halogen can be chloro, bromo or iodo; and
the monocyclic aryl or aralkyl are as exemplified above for (C₆ to C₉)aryl and (C₇ to C₁₃)aralkyl.

When one or more of the groups A, B, Y and Nu has/have reactive functional group/groups, such reactive group/groups can be protected for and during the terwards, the protecting groups can be removed by conventional deprotection procedures.

The compounds represented by Formula (I) can be prepared by a series of chemical processes which may be represented, for example, by the following reaction scheme;

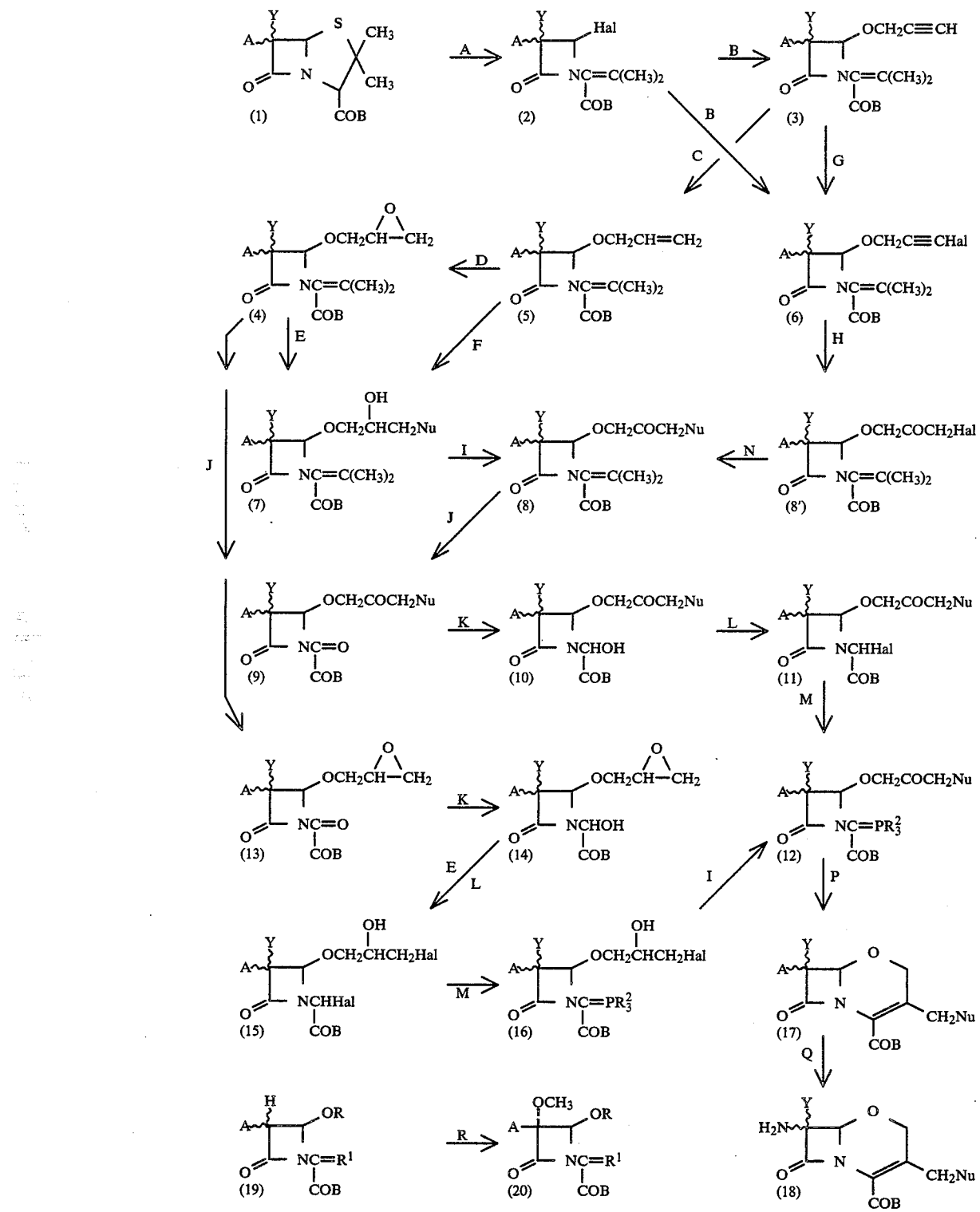

reactions involved in making the cephalosporin analogs which may be made from the present compounds. Afterwards, (wherein A, COB, Hal, Nu, R, R¹, R² and Y are as hereinbefore defined.)

The compound (18) can be modified in a conventional manner to give a compound (17), wherein A is acylamino and COB is carboxy or its equivalent, which is a strong antibacterial against gram positive and negative bacteria. For this purpose, the compound (18) has β-A, α-Y and optionally protected carboxy as COB. Other steroisomers at the 7-position are useful as intermediates for preparing said antibacterials.

Each unit process applicable to the above alignments of synthesis is given in the following sections A through R (excluding O) comprising general explanation, a few examples, list of reaction conditions if any, and tables showing physical constants of the products or compounds of this invention. Other combinations of the unit processes are applicable to achieve the same object, synthesis of compound (17) or (18). In such case, protective groups and reaction conditions can be introduced or changed for better protection of sensitive groups and deprotection.

A. PENAM CLEAVAGE

Penicillins are cleaved by the action of halogen to give α-(4-halo-3-acylamino-2-oxoazetidin-1-yl)-α-isopropylidenacetates. The process can be carried out by mixing halogen (e.g. chlorine) with a solution of penicilin or ester thereof in an inert solvent (e.g. chloroform, carbon tetrachloride) and stirring at −30° C. to 0° C. for 20 minutes to 3 hours.

EXAMPLE A

To a suspension of 2.18 g of diphenylmethyl 2,2-dimethyl-6α-phenylacetamidopenam-3α-carboxylate in 20 ml of chloroform is dropwise added a solution (9.5 ml; 17.5 mM) of chlorine in carbon tetrachloride at −20° C. to −30° C. with stirring. After about 30 minutes, the mixture gives a transparent yellow solution. This is washed with aqueous sodium hydrogen carbonate and saturated saline under ice cooling, dried over sodium sulfate, and evaporated to give diphenylmethyl α-(4β-chloro-3α-phenylacetamido-2-oxoazetidin-1yl)-α-isoproylideneacetate (2.4 g) as yellow material.

NMR: $\delta^{CDCl_3}$ 1.97s3H, 2.25s3H, 3.47s2H, 4.89dd(1;7 Hz)1H, 5.78d(1 Hz)1H, 6.55brd(7 Hz), 6.83s1H, 7.2 ml5H.

Similarly prepared is benzyl α-(4β-chloro-3α-phthalimido-2-oxoazetidin-1-yl)-α-isopropylideneacetate (NMR: $\delta^{CDCl_3}$ 2.20S3H, 2.47s3H, 5.40s2H, 5.63d(2 Hz)1H, 6.30d(2 Hz)1H, 7.36s1H, 7.46s5H, 7.74–8.15m4H) by treatment of 182 mg of benzyl 6α-phthalimidopenicillanate with 1.68 mM of chlorine in carbon tetrachloride at room temperature for 40 minutes.

B. ETHERIFICATION

This process comprises treatment of 4-halo-3-acylamino-2-oxoazetidin-1-acetic acids with propargyl alcohol optionally substituted by a halogen at the terminal acetylenic carbon in the presence of hydrogen halide acceptor (e.g. silver perchlorate, silver tetrafluoroborate) in the presence of absence of an inert solvent preferably at −30° C. to 30° C. for 0.5 to 5 hours.

EXAMPLE B

To a solution of 537 mg of diphenylmethyl α-(4β-chloro-3α-phenylacetamido-2-oxoazetidin-1-yl)-α-isopropylideneacetate in 3 ml of propargyl alcohol is added 500 mg of silver tetrafluoroborate at −23° C. with stirring. After 1 hour, benzene and an aqueous sodium hydrogen carbonate are added thereto, and the mixture is stirred for a while and then filtered. The benzene layer is worked up in a conventional manner to yield diphenylmethyl α-(4β-propargyloxy-3α-phenylacetamido-2-oxoazetidin-1-yl)-α-isopropylideneacetate.

Similarly prepared are 25 mg of benzyl α-(4β-propargyloxy-3α-phthalimido-2-oxoazetidin-1-yl)-α-isopropylideneacetate (NMR: $\delta^{CDCl_3}$ 5.38d(4 Hz)1H, 5.56d(4 Hz)1H) from 35 mg of benzyl α-(4β-chloro-3α-phthalimido-2-oxoazetidin-1-yl)-α-isopropylideneacetate, 60 mg of zinc chloride, 0.2 ml of propargyl alcohol and 16 μl of N-methylmorpholine at room temperature for 2 hours and diphenylmethyl α-(4β-propargyloxy-3β-phenylacetamido-3α-methoxy-2-oxoazetidin-1-yl)-α-isopropylideneacetate (NMR: $\delta^{CDCl_3}$ 1.98s3H, 2.16s 3H, 3.44s2H, 3.63brs3H, 4.01d(2 Hz)2H), 5.33s1H, 6.83brs1H, 6.98s1H, 7.32 ml5H) from the corresponding 4β-chloro compound, zinc chloride, propargyl alcohol, and N-methylmorpholine.

C. PARTIAL HYDROGENATION

This reduction is a conventional selective reduction of a triple bond to a double bond. Thus, for example, hydrogenation is carried out under a hydrogen atmosphere in a suitable solvent (e.g. an alcohol, ester, or aqueous solvent) under atmospheric or elevated pressure with a catalyst suitable for the selective hydrogenation (e.g. palladium on various carriers or a nickel catalyst, each being deactivated with e.g. such heavy metal salts as acetate or nitrate of lead. bismuth, or copper, or deactivated with acetone, pyridine, quinoline, or mercaptane) until about 1 mole of hydrogen is consumed. Other types of reduction (e.g. electro-reduction, diazine or metal-proton reduction) can also be used to effect this reduction.

EXAMPLE C

A solution of 1.0 g of diphenylmethyl α-[4β-(2-propynyl)oxy-3α-phenylacetamido-2-oxoazetidin-1-yl]-α-isopropylideneacetate in 10 ml of methanol is catalytically hydrogenated in hydrogen atmosphere with 0.25 g of 5% palladium-calcium carbonate catalyst. The product is worked up in a conventional manner to yield 0.88 g of diphenylmethyl α-[4β-allyloxy-3α-phenylacetamido-2-oxoazetidin-1-yl]-α-isopropylideneacetate (88% yield). m.p. 110°–112° C.

Similarly prepared are 11.8 g of diphenylmethyl α-(4β-allyloxy-3β-phenylacetamido-2-oxoazetidin-1-yl)-α-isopropylideneacetate (IR: $\nu_{max}^{CHCl_3}$ 3430, 1776, 1720, 1679, 1632, 1504 cm$^{-1}$) from 12.1 g of diphenylmethyl α-(4β-propargyloxy-3β-phenylacetamido-2-oxoazetidin-1-yl)-α-isopropylideneacetate in 50 ml of methanol and 500 ml of hydrogen in the presence of 5% palladium on calcium carbonate at room temperature for 1 hour; diphenylmethyl α-(4β-allyloxy-3β-carbobenzoxyamino-2-oxoazetidin-1-yl)-α-isopropylideneacetate from 26.5 g of diphenylmethyl α-(4β-propargyloxy-3β-carbobenzoxyamino-2-oxoazetidin-1-yl)-α-isopropylideneacetate (IR: $\nu_{max}^{CHCl_3}$ 3440, 1772, 1720, 1628, 1505 cm$^{-1}$) in 100 ml of methanol and 1180 ml of hydrogen in the presence of 6.6 g of 5% palladium on calcium carbonate at room temperature for 50 minutes; and diphenylmethyl α-(4β-allyloxy-3β-phenylacetamido-3α-methoxy-2-oxoazetidin-1-yl)-α-isopropylideneacetate (IR: $\nu_{max}^{CHCl_3}$ 1780, 1725, 1700, 1495 cm$^{-1}$) melting at 76°–77° C. from the corresponding 4β-propargylazetidinone compound, hydrogen, and palladium on calcium carbonate in methanol.

D. EPOXIDATION

This oxidation is an action of oxidizing reagent capable of forming epoxides from ethylene compounds. Suitable oxidizing reagents for this process include organic or inorganic oxidizing reagents having oxido-reduction potentials of at least +1.5 volt. Thus, for example, suitable reagents are organic or inorganic peracids, salts of organic or inorganic peracids, hydrogen peroxide, metal peroxides, and mixtures of hydrogen peroxide and an acid of dissociation constant at least $10^{-5}$ (e.g. acetic acid, formic acid, perchloric acid, trifluoroacetic acid, wolfrumates). Preferred organic peracids include percarboxylic acids and persulfonic acids (e.g. performic acid, peracetic acid, perpropionic acid, monopersuccinic acid, percamphoric acid, monoperphthalic acid, trifluoroperacetic acid, perbenzoic acid, m-chloro-perbenzoic acid, m-nitroperbenzoic acid and toluenepersulfonic acid) preferably in an inert solvent at 0° C. to 40° C. for 1 to 10 hours. Preferable inorganic peracids include periodic acid and persulfuric acid. Alternatively, the epoxidation can be carried out by treating a halohydrin with a base. A halohydrin as given under the title HALOHYDRIN FORMATION is treated with a base (e.g. organic base or inorganic base) preferably at 0° C. to 30° C. for 10 to 60 minutes to form the epoxide.

EXAMPLE D (1) Direct epoxidation.

To a solution of 0.88 g of diphenylmethyl α-(4β-allyloxy-3α-phenylacetamido-2-oxoazetidin-1-yl)-α-isopropylideneacetate in 9 ml of chloroform is added 0.54 g of m-chloroperbenzoic acid and allowed to stand at room temperature overnight. The reaction mixture is washed with an aqueous hydrogen sulfite solution, an aqueous sodium hydrogencarbonate solution, and then water, dried, and concentrated. The residue is chromatographed on 20 parts by volume of silica gel and eluted with a mixture of benzene and ethyl acetate (4:1) to yield 475 mg of diphenylmethyl α-[4β-(2,3-epoxypropoxy)-3α-phenylacetamido-2-oxoazetidin-1-yl)-α-isopropylideneacetate (51.7% yield). Crude starting material (147 mg; ca. 17%), m.p. 110°–112° C., is recovered.

(2) Via bromohydrin

To a solution of 148 mg diphenylmethyl α-(3α-phenylacetamido-4β-allyloxy-2-oxoazetidin-1-yl)-α-isopropylideneacetate in 2.0 ml of dimethyl sulfoxide and 0.1 ml of water is added 60 mg of N-bromoacetamide under ice cooling, and the mixture is stirred at room temperature for 1.5 hours and then ice cooled. To this mixture is added 80 mg of potassium t-butoxide, and the mixture is stirred at the same temperature for 20 minutes, mixed with water, and extracted with ethyl acetate. The extract is worked up in a conventional manner to yield 120 mg of diphenylmethyl α-[3α-phenylacetamido-4β-(2,3-epoxypropoxy)-2-oxoazetidin-1-yl]-α-isopropylideneacetate.

IR: $\nu_{max}^{CHCl_3}$ 3410, 1775, 1720, 1680 cm$^{-1}$. m.p. 114°–115° C.

Other reactions are given in Table D.

E. EPOXIDE FISSION

This fission comprises reaction of an epoxide with a nucleophilic reagent of the formula: HNu (wherein Nu is a nucleophilic group) or a reactive derivative thereof to give a secondary alcohol substituted by Nu at the adjacent position.

The nucleophilic reagents include hydrogen azide, thioureas, thioamides, alcohols (e.g. methanol, ethanol, isopropanol, butanol or benzyl alcohol), carboxlyic acids (e.g. acetic acid, propionic acid, phenylacetic acid, benzoic acid), thiols (e.g. methanethiol, ethanethiol, dimethylaminoethanethiol, thiophenol, dinitrothiophenol, phenylmethanethiol, methylimidazolethiol, dihydroimidazolethiol, pyridinethiol, tetrazolethiol, methyltetrazolethiol, butyltetrazolethiol, phenyltetrazolethiol, triazolethiol, thiadiazolethiol, methylthiadiazolethiol, indolethiol, thiazolethiol, benzothiazolethiol, thienylthiol, oxadiazolethiol, carboxymethylthiadiazolethiol, aminomethylthiadiazolethiol, aminothiadiazolethiol, carbalkoxymethyltetrazolethiol, t-butoxycarbonylmethyltetrazolethiol, diphenylmethoxycarbonylmethyltetrazolthiol, or nitrophenyltetrazolethiol), amines (e.g. diethylamine, aniline, or nitrotoluidine), and aromatic compounds containing nitrogen (e.g. triazole, pyridine, or pyridazine) and water. Suitable reactive derivatives of the nucleophilic reagents include alkali metal salts or alkaline earth metal salts (e.g. lithium, sodium, potassium, calcium or magnesium salts) and organic base salts (e.g. trimethylamine, N-methylmorpholine, or tetramethylammonium hydroxide).

These reagents may be brought into contact with the epoxide preferably at about $-10°$ C. to $100°$ C. for 10 minutes to 2 hours in a solvent giving the objective compounds according to conventional procedures. The reaction can be accelerated by a base producing an ionic species of Nu as well as proton and Lewis acid activating the epoxide ring.

EXAMPLE E

To a solution of 3.7 g of diphenylmethyl α-[4β-(2,3-epoxypropoxy)-3α-phenylacetamido-2-oxoazetidin-1-yl]-α-isopropylideneacetate in 100 ml of chloroform is added 10 ml of hydrogen bromide and the mixture is stirred for 15 minutes. The reaction mixture is washed with water, dried, and concentrated to yield 4.9 g of crude diphenylmethyl α-[4β-(3-bromo-2-hydroxypropoxy)-3α-phenylacetamido-2-oxoazetidin-1-yl]-α-isopropylideneacetate.

IR: $\nu_{max}^{CHCl_3}$ 3400, 1760, 1720, 1670 cm$^{-1}$.

Other reactions are given in Table E.

F. HALOHYDRIN FORMATION

The ethylene group can be converted to give the corresponding halohydrins by the action of a hypohalogenous acid source (e.g. N-halosuccinimide, N-haloacetamide, or hypohalites) in the presence of water preferably at 10° C. to 40° C. for 20 minutes to 3 hours, if required, in the presence of an inert solvent and acid catalyst.

EXAMPLE F

To a solution of 688 mg of diphenylmethyl α-(3α-methoxy-3β-phenylacetamido-4β-allyloxy-2-oxoazetidin-1-yl)-α-isopropylideneacetate in 7 ml of dry dimethylsulfoxide, to which 55 μl of water is added, is added 336 mg of N-bromosuccinimide in small portions at 15°

C. to 20° C., and the mixture is stirred at the same temperature for 1 hour. Ice water is added, and the mixture is extracted with a large amount of ethyl acetate. The extract is washed well with water, dried, and evaporated to yield 740 mg of diphenylmethyl α-[3α-methoxy-3β-phenylacetamido-4β-(2-hydroxy-3-bromopropyl)oxy-2-oxoazetidin-1-yl]-α-isopropylideneacetate as a colorless foamy material.

IR: $\nu_{max}^{CHCl_3}$ 3600–3200, 1775, 1720, 1690, 1060 cm$^{-1}$.

Similarly prepared are 116 mg of diphenylmethyl α-[4β-(3-chloro-2-hydroxypropoxy)-3α-phenylacetamido-2-oxoazetidin-1-yl]-α-isopropylideneacetate (IR: $\nu_{max}^{CHCl_3}$ 3400, 1775, 1720, 1680 cm$^{-1}$) from 108 mg of the corresponding 4β-allyloxyazetidinone compound, N-chlorosuccinimide, water, and dimethyl sulfoxide for 30 minutes at room temperature; and diphenylmethyl α-[4β-(3-bromo-2-hydroxypropoxy)-3α-phenylacetamido-2-oxoazetidin-1-yl]-α-isopropylideneacetate (IR: $\nu_{max}^{CHCl_3}$ 3400, 1760, 1720, 1670 cm$^{-1}$) from 1.05 g of the corresponding 4β-allyloxyazetidinone compound, 10 ml of dimethyl sulfoxide, 90 μl of water, and 537 mg of N-bromosuccinimide at room temperature for 1 hour.

G. ACETYLENE HALOGENATION

This process for introducing a halogen to acetylene carbon can be carried out by treating an acetylene compound with a halogenating reagent (e.g. pyridine halogenium salts) preferably in an inert solvent e.g. chloroform or methylene chloride at 10° C. to 70° C. for 1 to 5 hours.

EXAMPLE G

To an ice cooled and stirred solution of pyridine iodium nitrate in chloroform is added 2.09 g of diphenylmethyl α-[3α-phenylacetamido-4β-(2-propynyl)oxy-2-oxoazetidin-1-yl]-α-isopropylideneacetate. After 5 minutes, the mixture is warmed up to room temperature, stirred for 2 hours, and poured into cooled dilute hydrochloric acid. The chloroform layer is worked up in a conventional manner to yield 2.00 g of diphenylmethyl α-[3α-phenylacetamido-4β-(3-iodo-2-propynyl)oxy-2-oxoazetidin-1-yl]-α-isopropylideneacetate, m.p. 134°–137° C.

IR: $\nu_{max}^{CHCl_3}$ 3425, 2187, 1777, 1726, 1686, 1631, 1094 cm$^{-1}$.

Similarly prepared are diphenylmethyl α-[3β-phenylacetamido-4β-(3-bromopropargyl)oxy-2-oxoazetidin-1-yl]-α-isopropylideneacetate and diphenylmethyl α-[3α-phenylacetamido-4β-(3-bromopropargyl)oxy-2-oxoazetidin-1-yl]-α-isopropylideneacetate (IR: $\nu_{max}^{CHCl_3}$ 3410, 2218, 1777, 1722, 1693, 1632, 1603, 1587 cm$^{-1}$).

These compounds can also be produced by reaction B using bromopropargyl alcohol as the reagent.

H. HYDRATION

This process is carried out by treating an acetylene compound with water in the presence of a catalyst (e.g. mercuric sulfate, mercuric chloride, mercuric acetate) in an aqueous solvent (e.g. aqueous diluted sulfuric acid) preferably at −10° C. to 100° C. for 15 minutes to 3 hours.

EXAMPLE H

To a solution of 601 mg of diphenylmethyl α-[3α-phenylacetamido-4β-(3-bromo-2-propynyl)oxy-2-oxoazetidin-1-yl]-α-isopropylideneacetate in 95% aqueous methanol is added 7.7 ml of 10% sulfuric acid solution of 0.13 mole of mercury sulfate, and the mixture is refluxed under heating for 1 hour, evaporated under reduced pressure, mixed with ice water and extracted with methylene chloride. The extract is worked up in a conventional manner to yield diphenylmethyl α-[3α-phenylacetamido-4β-(3-bromo-2-oxopropyl)oxy-2-oxoazetidin-1-yl]-α-isopropylideneacetate (603 mg).

IR: $\nu_{max}^{CDCl_3}$ 3400, 1770, 1720, 1675 cm$^{-1}$.

Other reactions are given in Table H.

I. OXIDATION OF SECONDARY ALCOHOL

This process can be carried out by treating a secondary alcohol with an oxidizing reagent to give the corresponding ketone.

The oxidizing reagents can be a chromate, manganate, hypohalide, halogen, N-haloamide, N-haloimide, oxygen, dialkyl sulfoxide with an acid anhydride, cobaltic ions, pentavalent vanadium, cerium, aluminum alkoxide, persulfate, or dinitrogen tetraoxide, and can be used in various solvents for oxidation e.g. ester, ether, ketone, halohydrocarbon or hydrocarbon solvents or mixtures thereof. Chromium trioxide, especially so-called Jones reagent comprising of chromium trioxide in 6 to 10N sulfuric acid, is one of the most feasible oxidizing reagents for this purpose, which can preferably used at 0° C. to 10° C. for 5 minutes to 2 hours in a ketone solvent e.g. acetone or ether solvent e.g. dioxane.

EXAMPLE I

To a solution of 4.9 g of diphenylmethyl α-[4β-(3-bromo-2-hydroxypropoxy)-3α-phenylacetamido-2-oxoazetidin-1-yl]-α-isopropylideneacetate in 50 ml of acetone is added 5 ml of Jones reagent under ice cooling, and the mixture stirred at 0° C. for 30 minutes and then at room temperature for 30 minutes. Excess amount of the reagent is decomposed by the addition of isopropanol and the insoluble material is removed by filtration. The filtrate is worked up in a conventional manner to yield 4.75 g of crude diphenylmethyl α-[4β-(3-bromo-2-oxopropoxy)-3α-phenylacetamido-2-oxoazetidin-1-yl]-α-isopropylideneacetate.

IR: $\nu_{max}^{CHCl_3}$ 3400, 1770, 1720, 1675 cm$^{-1}$.

Other reactions are given in Table I.

J. OZONE CLEAVAGE

The process can be carried out by treating an unsaturated compound with a suitable oxidizing reagent to give the corresponding oxo compound. Representative oxidizing reagents include hexavalent chromium oxidizing reagent and a combination of glycol forming and glycol cleaving reagent. The most convenient reagent is ozone to form an oxidation product called ozonide in combination with a following treatment with a reducing reagent including inorganic reducing salts, hydrogen and catalysts, amalgam of reducing metals, reducing metals and acid, or reducing organic substances including formaldehyde, alkyl sulfides, phosphines, or phosphites.

The reaction can be carried out in a conventional manner preferably by bubbling ozone into a solution of a starting material in an inert solvent (e.g. haloalkane, alkanoic acid, or alkanoate solvent) preferably in the presence of an alkanol (e.g. methanol solvent) at −80° C. to −5° C. until blue color of ozone appears or satisfactory reaction is found by e.g. thin-layer chromatography, then followed by adding a reducing reagent (e.g. zinc or tin and acetic acid, or lower alkyl sulfide) for reductively cleaving the formed ozonide giving the objective oxo compound.

EXAMPLE J

Into a solution of 3.67 g of diphenylmethyl α-{4β-[3-(1-methyltetrazol-5-yl)thio-2-oxopropyl]oxy-3α-phenylacetamido-2-oxoazetidin-1-yl}-α-isopropylideneacetate in 56.4 ml of methylene chloride is introduced ozone at −60° C. until the color of the solution turns blue. The mixture is then mixed with 4.23 ml of dimethyl sulfide at the same temperature, stirred at room temperature for 1 hour, washed with water, dried, and evaporated under reduced pressure to yield 3.45 g of diphenylmethyl α-{4β-[3-(1-methyltetrazol-5-yl)thio-2-oxopropyl]oxy-3α-phenylacetamido-2-oxoazetidin-1-yl}-α-oxoacetate as foamy material.

IR: $\nu_{max}^{CHCl_3}$ 3400, 1823, 1748, 1708 cm$^{-1}$.

Other reactions are given in Table J.

K. REDUCTION OF OXO GROUP

This process is a conventional reduction of an oxo group to give the corresponding secondary alcohol. The reduction can be carried out by the action of a reducing reagent capable of reducing an oxo group to a secondary hydroxyl group. The reducing reagent can, for example, be a borohydride reducing reagent (e.g. borane, sodium borohydride, potassium borohydride, or sodium cyanoborohydride), hydrogen in the presence of a catalyst (e.g. palladium or platinum catalysts), an alkali metal alkoxyaluminum hydride or, most preferably metal (e.g. zinc, tin, iron, aluminum, or magnesium) and a protic substance (e.g. mineral acid, organic acid including formic acid and acetic acid, alcohol, or water).

The reaction can be carried out in a conventional manner in a solvent inert to the reaction, preferably with zinc and acetic acid at −30° C. to 100° C. for 15 minutes to 2 hours.

EXAMPLE K

To a solution of 3.45 g of diphenylmethyl α-{4β-[3-(1-methyltetrazol-5-yl)thio-2-oxopropyl]oxy-3α-phenylacetamido-2-oxoazetidin-1-yl}-α-oxoacetate in 15 ml of methylene chloride is added 15 ml of acetic acid. The mixture is stirred with 5.4 g of activated zinc powder under ice cooling for 35 minutes, then stirred with a further 2.0 g of zinc powder at 13° C. for 20 minutes. Solid material is filtered off, and the filtrate is washed with water, dried, and evaporated under reduced pressure to give 3.30 g of diphenylmethyl α-{4β-[3-(1-methyltetrazol-5-yl)thio-2-oxopropyl]oxy-3α-phenylacetamido-2-oxoazetidin-1-yl}-α-hydroxyacetate.

IR: $\nu_{max}^{CHCl_3}$ 3550–3200, 1786, 1750, 1678, 1100 cm$^{-1}$.

Other reactions are given in Table K.

L. HALOGENATION OR SULFONYLATION

This process is carried out by contacting a hydroxy compound with a conventional halogenating reagent capable of substituting a hydroxyl group with a halogen atoms (e.g. a phosphorus trihalide, pentahalide, or oxyhalide, a thionyl halide, an oxalyl halide, or a hypohalogeneous acid or its salts) preferably in an inert solvent and in the presence of an acid receptor at −10° C. to 40° C. for 15 minutes to 3 hours to give the corresponding halo compound.

Alternatively, a hydroxy compound is treated with a sulfonic acylating reagent (e.g. an alkyl or aryl-sulfonyl halide) in the presence of an acid receptor at −20° C. to 40° C. for 15 to 3 hours to give the corresponding sulfonyloxy compound.

EXAMPLE L

To a solution of 3.30 g of diphenylmethyl α-{4β-[3-(1-methyltetrazol-5-yl)thio-2-oxopropyl]oxy-3α-phenylacetamido-2-oxoazetidin-1-yl}-α-hydroxyacetate in 35 ml of methylene chloride are added 0.48 ml of thionyl chloride and 0.45 ml of pyridine with stirring under ice-cooling, and the mixture is stirred for 30 minutes. The reaction mixture is washed with water, dried and evaporated under reduced pressure to yield 3.37 g of diphenylmethyl α-{4β-[3-(1-methyltetrazol-5-yl)thio-2-oxopropyl]oxy-3α-phenylacetamido-2-oxoazetidin-1-yl}-α-chloroacetate as foamy material.

IR: $\nu_{max}^{CHCl_3}$ 3420, 1800, 1760, 1680 cm$^{-1}$.

Other reactions are given in Table L.

M. PHOSPHORANYLIDENE INTRODUCTION

A halo compound is treated with a phospine of the formula PR$^2_3$ (wherein R$^2$ is an optionally substituted alkyl or aryl) to give the corresponding phosphoranilidene compound, when carried out in the presence of a base (e.g. pyridine).

The phosphine can, for example, be bis(2-cyanoethyl)phenylphosphine, tri(chlorophenyl)phosphine, tricyclohexylphosphine, bisdiphenylphosphinylmethane, tri-n-butylphosphine, triethylphosphine, tri-n-octylphosphine, triphenylphosphine, tritolylphosphine, or trimethoxyethylphosphine. Triphenylphosphine is the most useful reagent for this purpose, as this group to be introduced is removed in a later stage of synthesis and no complex structure is essential.

The reaction can be carried out in an inert solvent e.g. toluene, benzene, chloroform, tetrahydrofuran, or dioxane, and preferably at 30° C. to 120° C. for 1 to 10 hours.

EXAMPLE M

To a solution of 3.37 g of diphenylmethyl α-{4β-[3-(1-methyltetrazol-5-yl)thio-2-oxopropyl]oxy-3α-phenylacetamido-2-oxoazetidin-1-yl}-α-chloroacetate in 35 ml of dry methylene chloride is added 4.41 g of triphenylphosphine, and the mixture is heated under reflux in nitrogen atmosphere for 4 hours. The reaction mixture is then poured into a mixture of 100 ml of ice-water and 10 ml of 5% sodium hydrogencarbonate aqueous solution, and extracted with methylene chloride. The extract is washed with water, dried, and evaporated to dryness under reduced pressure. The residue is chromatographed on silica gel to give 2.09 g of diphenylmethyl α-{4β-[3-(1-methyltetrazol-5-yl)thio-2-oxopropyl]oxy-3α-phenylacetamido-2-oxoazetidin-1-yl}-α-triphenylphosphoranylideneacetate.

Other reactions are given in Table M.

N. NUCLEOPHILE EXCHANGE

This process can be effected by substituting a leaving Nu group with a nucleophile having the desired nucleophilic group to give the objective compound having desired Nu group. Thus, for example, a compound where Nu is halogen may be treated with an alkali metal heteroaromatic thiolate to give the corresponding compound wherein Nu is a heteroaromatic thio group. The reaction can preferably be carried out at −10° C. to 40° C. for 10 minutes to 3 hours in an inert solvent.

EXAMPLE N

To a solution of 603 mg of diphenylmethyl α-[3α-phenylacetamido-4β-(3-bromo-2-oxopropyl)oxy-2-oxoazetidin-1-yl]-α-isopropylideneacetate and 124 mg of 5-mercapto-1-methyltetrazole in 6 ml of acetone is added 135 μl of triethylamine under ice cooling, and the mixture stirred for 30 minutes. The reaction mixture is diluted with ice water and extracted with methylene chloride. The extract is worked up in a conventional manner to yield 161 mg of diphenylmethyl α-[3α-phenylacetamido-4β-{3-(1-methyltetrazol-5-yl)thio-2-oxopropyl}-oxy-2-oxoazetidin-1-yl)-α-isopropylideneacetate.

Other reactions are given in Table N.

P. CYCLIZATION

This process is an intramolecular Wittig reaction.

The reaction can be carried out by warming a phosphoranylidene compound having an oxo group at a suitable position in an inert solvent e.g. dioxane, tetrahydrofuran, benzene or dichloromethane) at 50° C. to 100° C. for from 5 to 20 hours.

EXAMPLE P

A solution of 2.09 g of diphenylmethyl α-{4β-[3-(1-methyltetrazol-5-yl)thio-2-oxopropyl]oxy-3α-phenylacetamido-2-oxoazetidin-1-yl}-α-triphenylphosphoranylideneacetate in 20 ml of dioxane is refluxed for 17 hours under nitrogen gas. Solvent is removed by evaporation under reduced pressure, and the residue is purified by silica gel chromatography to yield 0.688 g of (6R, 7S)-diphenylmethyl 3-(1-methyltetrazol-5-yl)thiomethyl-7α-phenylacetamido-1-dethia-1-oxa-3-cephem-4-carboxylate as crystals melting at 100° C. to 105° C.

IR: $\nu_{max}^{CHCl_3}$ 3400, 1790, 1718, 1685 cm$^{-1}$.
$[\alpha]_D^{22}$ −193.2° (c=0.263CHCl$_3$).

Other reactions are given in Table P.

Q. DEACYLATION

The acyl group of an acylamino-1-dethia-1-oxa-3-cephem-4-carboxylic acid can be removed conveniently according to conventional methods.

The most preferable one consists of (1) dissolving the starting material in an inert solvent (e.g. methylene chloride or chloroform) and stirred with an iminohalogenating reagent (e.g. phosphorus pentachloride) in the presence of a base (e.g. pyridine) at low temperature (e.g. −50° C. to 0° C.) for 0.5 to 5 hours; (2) diluting with excess amount of an alcohol (e.g. methanol, ethanol, or isobutanol) and keeping at 0° C. to 40° C. for 0.5 to 5 hours; and (3) treating with water for 5 to 60 minutes at room temperature. The last step can be omitted when the following work-up utilizes water.

EXAMPLE Q

To a solution of 500 mg of diphenylmethyl 1-dethia-1-oxa-3-(1-methyltetrazol-5-yl)thiomethyl-7α-phenylacetamido-3-cephem-4-carboxylate in 12 ml of dry methylene chloride are added 0.136 ml of pyridine and 0.349 g of phosphorus pentachloride at −20° C., and the mixture is stirred at the same temperature for 30 minutes and then at room temperature for 25 minutes. The reaction mixture is stirred with 6.0 ml of anhydrous methanol at −20° C. and at room temperature for 1 hour. Water (2.67 ml) is added, and the mixture is poured into 15 ml of 5% sodium hydrogencarbonate and 50 ml of ice water, and extracted with methylene chloride. The extract is washed with water, dried, and evaporated to dryness under reduced pressure. The residue is chromatographed on silica gel to give 333 mg of diphenylmethyl 1-oxadethia-3-(1-methyltetrazol-5-yl)thiomethyl-7α-amino-3-cephem-4-carboxylate as foamy material.

IR: $\nu_{max}^{CHCl_3}$ 3380, 1785, 1720 cm$^{-1}$.

Other reactions are given in Table Q.

R. METHOXYLATION

The methoxylation of an α-(3-acylamino-4-OR-2-oxoazetidin-1-yl)-α-substituted acetic acid and its derivatives can be carried out in various methods. The most convenient one is to halogenate at the amido nitrogen with 1 to 2 mole equivalent of hypohalogenous halogenating reagent (e.g. t-butyl hypochlorite) at low temperature (e.g. at −50° C. to 0° C.), and then 1 to 2 mole equivalents of alkali metal methoxide (e.g. lithium methoxide) in methanol at the same temperature to give the desired 3α-methoxy compound in high yield.

EXAMPLE R

To a solution of 139 mg of diphenylmethyl α-(3α-phenylacetamido-4β-propargyloxy-2-oxoazetidin-1-yl)-α-isopropylideneacetate in 2.7 ml of methylene chloride cooled to −40° C. are added 48 μl of t-butyl hypochlorite and then a solution of lithium methoxide in methanol (2 Mole/l), and the mixture is stirred for about 40 minutes. The mixture is then slightly acidified with about 20 μl of acetic acid, diluted with methylene chloride, washed with water, an aqueous solution of sodium hydrogencarbonate, an aqueous sodium sulfite, and a saturated saline, dried, and evaporated under reduced pressure to give 144 mg of diphenylmethyl α-(3α-methoxy-3β-phenylacetamido-4β-propargyloxy-2-oxoazetidin-1-yl)-α-isopropylideneacetate.

NMR: $\delta^{CDCl_3}$ 1.98s3H, 2.16s3H+1H, 3.44s3H, 3.63brd2H, 4.01d(2 Hz)2H, 5.33s1H, 6.83brs1H, 6.98s1H, 7.32 ml5H.

Other reactions are given in Table R.

For the preparation of antibacterially active 1-oxadethiacephalosporins (17), 4β-OR in the intermediates is essential. In the primary research, a compound (2) having 3β-NH$_2$, 3α-hydrogen as Y, and 4-Hal was used as starting materials giving an epimer mixture (up to about 1:1) at the 4-position (3). The inventors assumed introduction of OR occurs predominantly from trans side of group A, and succeeded in proving this assumption by showing 4β-OR introduction when A is in the 3α-position. By using 3α-A starting material (2), the yield of the desired 4β-etherification giving (2) is very much ameliorated. As 3α-A intermediates are well converted into 3β-A, 3α-Y derivatives in any process of a series of processes given above, desired final products (17) is obtained from Compounds (1) in better overall yield when compared with the processes through 3β-A fixed reactions. It is to be noted that inversion of the substituent at the 3-poxition of azetidinone intermediates can be achieve to give the antibacterially preferable 7β-A series of 1-oxadethiacephem compounds. This process using the 3α-A series is one aspect of this invention.

Introduction of a Nu group has never been reported in detail. The applicant filed an application for giving 1-oxadethiacephalosporins corresponding to Compounds (17) provided that Nu is hydrogen, but it took long time of research to reduce the concept to practice, as the methods and intermediates in the process had been unknown. Now, the inventors successfully introduced the group Nu in several ways as hereinabove described for preparing more effective 1-oxadethiacephalosporins (17). This introduction of Nu and succeeding treatments for giving the objective Compounds (17) constitutes another part of this invention.

Introduction of methoxy as Y at the 3α-position to give Compounds (20) from (19) was found to proceed as in the case of penicillins and cephalosporins, in spite of lacking the additional five or six membered ring which is present in the case of those antibiotics. This methoxylation is another process of this invention.

A series of reactions starting from Compounds (20) to give Compounds (17) is further aspect of this invention.

The following Tables are given to show some variation of the specific examples of the processes given above in detail. They show general applicability of the processes to make compounds of this invention.

In the Tables, many abbreviations are used for simplicity and easy understanding. They are listed below for reference and consisting mainly of those traditional among those skilled in the art.

| Ac | = acetyl |
|---|---|
| An | = acetone |
| B | = benzamido |
| BH | = diphenylmethoxycarbonyl |
| Bu | = butyl |
| BZ | = benzyloxycarbonyl |
| CBz | = benzyloxycarbonylamino |
| m-CPBA | = m-chloroperbenzoic acid |
| Di | = dioxane |
| DMSO | = dimethylsulfoxide |
| Et | = ethyl |
| G | = phenylacetamido |
| hr | = hour |
| Me | = methyl |
| min. | = minute |
| NBS | = N—bromosuccinimide |
| Ph | = phenyl |
| refl. | = refluxing temperature |
| rt | = room temperature |
| S.M. | = starting material |
| TDAZ | = 1,3,4-thiadiazole ring |
| TETR | = tetrazole ring |
| Temp. | = temperature |
| THF | = tetrahydrofuran |

Then follow listed physical constants of the products. Some products have no cited constants, but they are identified after succeeding process(es) implying correct structure assigned. This is a result of mere convenience of experiments in laboratory, and in accordance with scientific traditions. When amorphous, m.p. shows softing point.

TABLE D (Epoxidation)

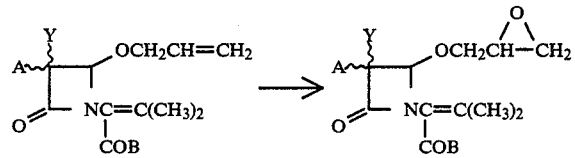

| Ex. No. | A | Y | COB | S.M. (g) | Solvent (ml) | Reagent (g) | | Temp. (°C.) | Time (min.) | | Temp. (°C.) | Time (hr) | Crop (g) |
|---|---|---|---|---|---|---|---|---|---|---|---|---|---|
| (1) Direct epoxidation. | | | | | | | | | | | | | |
| 1 | βG | αH | BH | 5.77 | CHCl₃ (60) | m-CPBA | (2.85) | | | | rt | 48 | 4.54 |
| 2 | βCbz | αH | BH | 25.6 | CHCl₃ (260) | m-CPBA | (15.3) | | | | rt | 48 | 21.25 |
| 3 | αG | ·βH | BH | 0.88 | CHCl₃ (9) | m-CPBA | (0.54) | | | | rt | 13 | 0.475 |
| (2) through bromohydrin. | | | | | | halohydrin formation | | | | epoxidation | | | |
| 4 | βG | αMeO | BH | 4.90 | DMSO (20) | NBS (2.4) | H₂O (1.0) | rt | 90 | t-BuOK (—) | rt | 0.3 | 0.12 |
| 5 | αB | βH | BH | 14.8 | DMSO (130) | NBS (10.4) | H₂O (6.5) | 20 | 60 | t-BuOK (5.31) | 20 | 1 | 13.0 |
| 6 | αG | βH | BH | 0.148 | DMSO (2) | NBS (0.06) | H₂O (0.1) | rt | 90 | t-BuOK (0.08) | 0 | 0.3 | 0.12 |

TABLE E (Epoxide Fission)

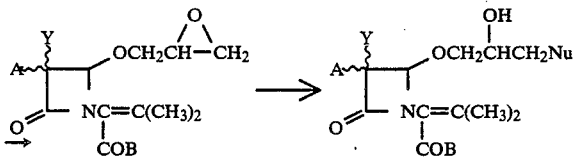

| Ex. No. | A | Y | COB | Nu | S.M. (g) | Solvent (ml) | HNu (g) | Catalyst (ml) | Temp. (°C.) | Time (min.) | Crop (g) |
|---|---|---|---|---|---|---|---|---|---|---|---|
| 1 | αG | βH | BH | —Cl | 0.108 | CHCl₃ (3) | 35% HCl (0.3 ml) | — | rt | 30 | 0.116 |
| 2 | αG | βH | BH | —Br | 3.7 | CHCl₃ (100) | HBr (10 ml) | — | rt | 15 | 4.9 |
| 3 | αG | βH | BH | —S—5-TETR-1-Me | 8.22 | THF (40) | 1.97NBuLi (1.54) | | rt | — | 10.35 |
| 4 | αG | βH | BH | —OAc | 1.08 | HOAc (10) | BF₃Et₂O (0.05) | | rt | 30 | 1.38 |
| 5 | βG | αMeO | BH | —Br | 0.688 | DMSO (7) | NBS (0.336) | H₂O (0.01) | rt | 60 | 0.74 |
| 6 | βG | αMeO | BH | —S—5-TETR-1-Me | 3.287 | THF (20) | 1.97NBuLi (0.64) | | rt | 180 | 3.82 |
| 7 | βG | αH | BH | —S—5-TETR | 16.22 | THF (200) | 3.63 | H₂SO₄ (0.5) | 0 | 240 | 21.05 |
| 8 | βG | αH | BH | —S—5-TETR-1-isoBu | 5.40 | THF (50) | 1.74 | BuLi (2 mMole) | rt | 360 | 7.10 |

4,592,865

TABLE E-continued
(Epoxide Fission)

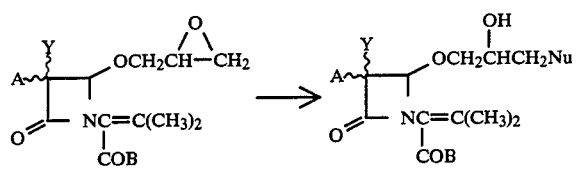

| Ex. No. | A | Y | COB | Nu | S.M. (g) | Solvent (ml) | HNu (g) | Catalyst (ml) | Temp. (°C.) | Time (min.) | Crop (g) |
|---|---|---|---|---|---|---|---|---|---|---|---|
| 9 | βG | αH | BH | —S—5-TETR-1-Ph | 5.41 | THF (80) | 2.14 | BuLi (7.22) | rt | 150 | 4.45 |
| 10 | βG | αH | BH | —S—5-TETR-1-CH₂COOH | 19.13 | THF (250) | 6.8 | $H_2SO_4$ (0.2) | 0 | 120 | 28.97 |
| 11 | βG | αH | BH | —S—5-TDAZ-2-Me | 1.50 | THF (20) | 0.44 | BuLi (3.32 mMole) | rt | 60 | 1.89 |
| 12 | βG | αH | BH | —OMe | 3.06 | MeOH (20) | — | $H_2SO_4$ (0.2) | 0 / rt | 15 / 60 | 2.99 |
| 13 | βG | αH | BH | —OAc | 2.50 | HOAc (17) | — | NaOAc (1.2 g) | 55 60 | 300 | 2.61 |
| 14 | βG | αH | BH | —Cl | 0.70 | CHCl₃ (16) | — | 35% HCl (4 ml) | rt | 15 | 0.46 |
| 15 | βG | αH | BH | —OH | 8.87 | An (90) | 18 | 30% HClO₄ (27) | rt | 150 | 8.5 |
| 16 | βG | αH | BH | —OH | 21.25 | An (220) | 44 | 30% HClO₄ (66) | rt | 180 | 20.6 |
| 17 | βG | αH | BH | —S—5-TETR-1-Me | 10.8 | THF (100) | 2.8 | 1.97BuLi (2) | rt | 360 | 13.1 |
| 18 | βB | αMeO | BZ | —S—5-TETR-1-Me | 10.50 | THF (95) | 3.05 | 1.6NBuLi (2.75) | 20 | 240 | 12.25 |

TABLE H
(Hydration)

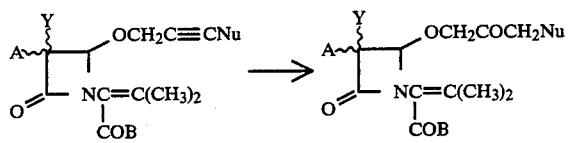

| Ex. No. | A | Y | COB | Nu | S.M. (g) | Solvent (ml) | Hg-salt (ml) | Temp. (°C.) | Time (min.) | Crop (g) |
|---|---|---|---|---|---|---|---|---|---|---|
| 1 | αG— | βH— | BH | —H | 0.5 | H₂O (1) | HgSO₄ (0.52) C₅H₁₁N (5) | rt | 14 | 0.176 |
| 2 | αG— | βH— | BH | —Br | 0.601 | 95% MeOH | 0.13M HgSO₄ | refl. | 60 | 0.603 |
| 3 | αG— | βH— | BH | —I | 0.324 | 90% MeOH (30) | 0.13M HgSO₄ | refl. | 70 | 0.327 |
| 4 | βG— | αMeO | BH | —Br | 0.192 | 97% MeOH (20) | 0.13M HgSO₄ | refl. | 50 | 0.176 |

TABLE I
(Oxidation of Secondary alcohol)

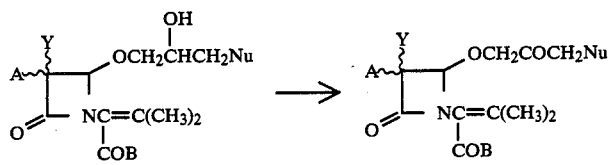

| Ex. No. | A | Y | COB | Nu | S.M. (g) | An (ml) | Jones reagent (ml) | Temp. (°C.) | Time (min.) | Crop (g) |
|---|---|---|---|---|---|---|---|---|---|---|
| 1 | αG | βH | BH | —Cl | 0.116 | 5 | 0.15 | rt | 60 | 0.112 |
| 2 | " | " | " | —Br | 1.274 | 10 | 1 | 0 | 180 | 1.226 |
| 3 | " | " | " | —S—5-TETR-1-Me | 9.8 | 100 | 13 | 0 / rt | 120 / 120 | 9.19 |
| 4 | " | " | " | —OAc | 1.38 | 25 | 1.2 | rt | 60 | 0.525 |
| 5 | " | " | " | —Br* | 1.17 | 20 | 1.5 | " | 90 | 0.95* |
| 6 | βG | αMeO | " | —S—5-TETR-1-Me | 3.82 | 35 | 5 | " | 60 | 2.975 |
| 7 | " | " | " | —Br* | 0.444 | 4 | 0.4 | 0 | 150 | 0.434* |
| 8 | " | αH | " | —S—5-TETR | 21.05 | 200 | 25 | rt | 90 | 11.07 |
| 9 | " | " | " | —S—5-TETR-2-Me | 2.03 | 20 | 1.8 | " | 90 | 2.02 |
| 10 | " | " | " | —S—5-TETR-1-isoBu | 7.10 | 75 | 6.5 | " | 90 | 6.1 |
| 11 | " | " | " | —S—5-TETR-1-Ph | 4.45 | 50 | 4.5 | " | 90 | 3.92 |
| 12 | " | " | " | —S—5-TETR-1-CH₂COOH | 15.9 | 190 | 16 | " | 180 | 2.6 |
| 13 | " | " | " | —S—5-TETR-1-CH₂COOt-Bu | | | | | | 0.78 |

TABLE I-continued (Oxidation of Secondary alcohol)

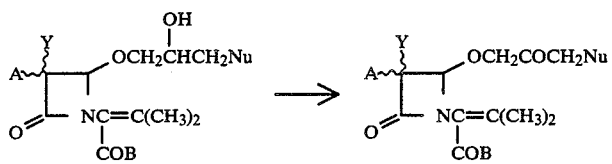

| Ex. No. | A | Y | COB | Nu | S.M. (g) | An (ml) | Jones reagent (ml) | Temp. (°C.) | Time (min.) | Crop (g) |
|---|---|---|---|---|---|---|---|---|---|---|
| 13 | | | | —S—5-TETR-2-CH$_2$COOt-Bu | 5.5 | 40 | 5 | " | 90 | 1.92 |
| 14 | " | " | " | —S—5-TDAZ-2-Me | 1.89 | 15 | 1.5 | " | 180 | 1.17 |
| 15 | " | " | " | —OMe | 2.98 | 30 | 3.0 | " | 120 | 2.0 |
| 16 | " | " | " | —OAc | 2.60 | 50 | 2.0 | " | 120 | 2.0 |
| 17 | " | " | " | —Cl | 0.40 | 7 | 4 equivalents | " | 220 | 0.3 |
| 18 | " | " | " | —S—5-TETR-1-Me | 14.1 | 150 | 13 | " | 90 | 12.4 |
| 19 | βB | αMeO | BZ | " | 12.2 | 210 | 12.6 | 20 | 60 | 11.24 |
| 20 | " | " | " | —Br | 3.53 | 141 | 2.82 | 0 | 60 | 3.24 |
| 21 | βG | αH | BH | —Cl* | 0.15 | 3 | 0.05 | rt | 60 | 0.14* |

*The reactions are for triphenylphosphoranylideneacetic acids instead of isopropylideneacetic acids.

TABLE J (Ozone cleavage)

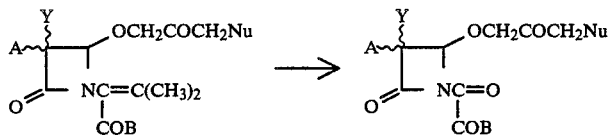

| Ex. No. | A | Y | COB | Nu | S.M. (g) | CH$_2$Cl$_2$ (ml) | Temp. (°C.) | Time (min.) | Reducing reagent(ml) | Temp. (°C.) | Time (min.) | Crop* (g) |
|---|---|---|---|---|---|---|---|---|---|---|---|---|
| 1 | αG | βH | BH | —OAc | 0.60 | 12 | −78 | — | Me$_2$S(1) | −78 / rt | 30 / 30 | 0.617 |
| 2 | " | " | " | " | 0.380 | 10 | " | — | Me$_2$S(1.6) | rt | 45 | 0.395** |
| 3 | " | " | " | —S—5-TETR-1-Me | 3.67 | 56 | −60 | — | Me$_2$S(4.2) | " | 60 | 3.45 |
| 4 | " | " | " | —S—5-TETR-1-Me | 1.63 | 20 | −78 | 30 | Zn(4.8 g) / HOAc(4) | −15 | 25 | (1.62) |
| 5 | " | " | " | —S—5-TETR-1-Me | 1.21 | 65 | " | — | Zn(3.6 g) / HOAc(14) | −20 | 35 | (1.113)*** |
| 6 | βG | αMeO | " | —S—5-TETR-1-Me | 0.397 | 4 | " | 30 | Zn(1.2 g) / HOAc(1) | −10 | 30 | (0.352) |
| 7 | " | αH | " | —S—5-TETR | 5.50 | 50 | " | 30 | Me$_2$S(5) | −78 / rt | 30 / 30 | 5.56 |
| 8 | " | " | " | —S—5-TETR-2-Me | 2.02 | 50 | " | 15 | Me$_2$S(2.5) | −78 / rt | 30 / 30 | 2.00 |
| 9 | " | " | " | —S—5-TETR-1-isoBu | 5.83 | 117 | " | 20 | Me$_2$S(6) | −78 / rt | 90 / 60 | 6.60 |
| 10 | " | " | " | —S—5-TETR-1-Ph | 3.92 | 50 | " | 25 | Me$_2$S(5) | −78 / rt | 30 / 30 | 3.87 |
| 11 | " | " | " | —S—5-TETR-1-CH$_2$BH | 2.60 | 70 | " | 15 | Me$_2$S(5) | rt | 20 | 2.50 |
| 12 | " | " | " | —S—5-TETR-1-CH$_2$COOt-Bu | 0.76 | 20 | " | — | Me$_2$S(1) | −78 / rt | 30 / — | 0.71 |
| 13 | " | " | " | —S—5-TETR-2-CH$_2$COOt-Bu | 2.11 | 40 | " | — | Me$_2$S(2) | −78 / rt | 30 / 30 | 1.93 |
| 14 | " | " | " | —S—5-TDAZ-2-Me | 1.17 | 30 | " | 10 | Me$_2$S(2) | −78 / rt | 30 / 30 | 1.10 |
| 15 | " | " | " | —OMe | 2.00 | 40 | " | 15 | Me$_2$S(3) | −78 / rt | 30 / 30 | 1.96 |
| 16 | " | " | " | —OAc | 2.00 | 30 | " | — | Me$_2$S(3) | −78 | 30 | 1.80 |

TABLE J-continued
(Ozone cleavage)

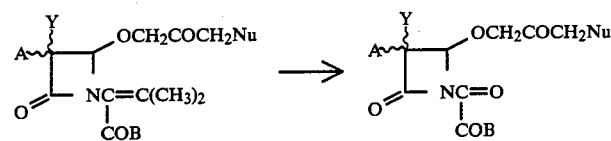

| Ex. No. | A | Y | COB | Nu | S.M. (g) | CH$_2$Cl$_2$ (ml) | Temp. (°C.) | Time (min.) | Reducing reagent(ml) | Temp. (°C.) | Time (min.) | Crop* (g) |
|---|---|---|---|---|---|---|---|---|---|---|---|---|
| 17 | " | " | " | —S—5-TETR-1-Me | 5.20 | 80 | " | — | Me$_2$S(6) | rt / −78 / rt | 30 / — / — | 4.99 |
| 18 | " | " | " | 4-substituent = 2,3-epoxy-propoxy | 1.50 | 40 | " | 17 | Me$_2$S(3) | −78 / rt | 30 / 30 | 1.51 |
| 19 | βB | αMeO | BZ | —S—TETR-1-Me | 11.2 | 112 | −60 | — | Zn/HOAc | −60 to rt | | (10.2) |
| 20 | " | " | " | 4-substituent = 2,3-epoxy-propoxy | 11.5 | 160 | −70 | — | Zn/HOAc | 0 | 80 | (10.36) |

*The values in parentheses show crops of glycolates produced by simultaneous reduction (Process K).
**Starting material has H$_2$C= group in place of oxo in the substituent at the position 4.
***Starting material has MeOOCCH= group in place of oxo in the substituent at the position 4. The reaction is carried out in the presence of 3.5 ml of methanol.

TABLE K
(Reduction of oxo group)

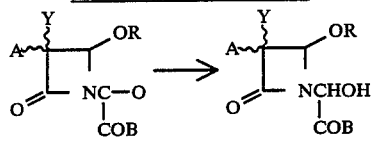

| Ex. No. | A | Y | COB | R | S.M.* (g) | CH$_2$Cl$_2$ (ml) | Zn (g) | HOAc (ml) | Temp. (°C.) | Time (min.) | Crop (g) |
|---|---|---|---|---|---|---|---|---|---|---|---|
| 1 | αG | βH | BH | —CH$_2$CH—CH$_2$ (O) | (0.324) | 7.5 | 1 | 1.5 | −15~−10 | 30 | 0.306 |
| 2 | " | " | " | —CH$_2$CCH$_2$S—5-TETR—1-Me ‖ CHCOOMe | (1.21) | 65 | 3.6 | 14 | −25~−17 | 35 | 1.113** |
| 3 | " | " | " | —CH$_2$COCH$_2$S—5-TETR—1-Me | (1.63) | 20 | 4.8 | 4 | −15~−10 | 30 | 1.62 |
| 4 | " | " | " | " | 3.45 | 15 | 7.4 | 15 | 0~13 | 55 | 3.30 |
| 5 | " | " | " | —CH$_2$COCH$_2$OAc | 7.4 | 80 | 8 | 80 | 0 | 30 | 7.9 |
| 6 | " | " | " | " | 0.617 | 6 | 1.2 | 6 | 0 | 60 | 0.576 |
| 7 | βG | αMeO | " | —CH$_2$COCH$_2$S—5-TETR—1-Me | (0.397) | 5 | 1.2 | 1 | −10 | 30 | 0.352 |
| 8 | " | αH | " | —CH$_2$COCH$_2$S—5-TETR | 5.56 | 15 | 15 | 15 | 0 | 180 | 5.16 |
| 9 | " | " | " | —CH$_2$COCH$_2$S—5-TETR—2-Me | 2.0 | 7 | 4 | 7 | " | 120 | 1.71 |
| 10 | " | " | " | —CH$_2$COCH$_2$S—5-TETR—1-isoBu | 6.60 | 24 | 11.1 | 24 | " | 435 | 5.3 |
| 11 | " | " | " | —CH$_2$COCH$_2$S—5-TETR—1-Ph | 3.87 | 15 | 7.7 | 15 | " | 120 | 3.91 |
| 12 | " | " | " | —CH$_2$COCH$_2$S—5-TETR—1-CH$_2$COOt-Bu | 0.71 | 3 | 3 | 3 | " | 180 | 0.69 |
| 13 | " | " | " | —CH$_2$COCH$_2$S—5-TETR—2-CH$_2$COOt-Bu | 1.87 | 8 | 7 | 8 | 0 / rt | 60 / 7 | 1.75 |
| 14 | " | " | " | —CH$_2$COCH$_2$S—5-TDAZ—2-Me | 0.83 | 3.5 | 3 | 3.5 | 0 / rt | 20 / 30 | 0.80 |
| 15 | " | " | " | —CH$_2$COCH$_2$OMe | 1.96 | 8 | 3 | 8 | 0 / rt | 30 / 210 | 1.81 |
| 16 | " | " | " | —CH$_2$COCH$_2$OAc | 1.80 | 10 | 5 | 10 | rt | 30 | 1.85 |
| 17 | " | " | " | —CH$_2$CH—CH$_2$ (O) | 0.42 | 1 | 0.6 | 1 | 0 / rt | 30 / 60 | 0.40 |
| 18 | " | " | " | —CH$_2$COCH$_2$S—5-TETR—1-Me | 2.05 | 8 | 3 | 8 | 0 | 80 | 2.05 |
| 19 | βB | αMeO | BZ | " | (11.2) | 149 | 33.6 | 30 | 0 | — | 10.2 |

TABLE K-continued
(Reduction of oxo group)

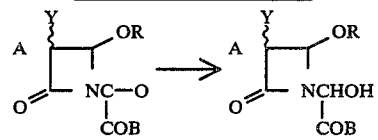

| Ex. No. | A | Y | COB | R | S.M.* (g) | CH₂Cl₂ (ml) | Zn (g) | HOAc (ml) | Temp. (°C.) | Time (min.) | Crop (g) |
|---|---|---|---|---|---|---|---|---|---|---|---|
| 20 | " | " | " | —CH₂CH——CH₂ \\O/ | (11.5) | 240 | — | 160 | 0 | 80 | 10.36 |

*The values in parentheses are those of isopropylideneacetic acids which is subjected to reaction J to give the starting material of this reaction, then without isolation, it is treated by a required reagent of this reaction.
**The product has R being —CH₂COCH₂S—5-TETR—1-Me, and the =CHCOOMe group is removed during the ozonization leaving an oxo group.

TABLE L
(Halogenation and sulfonylation)

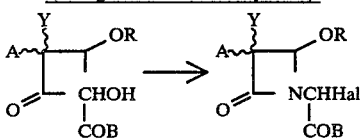

| Ex. No. | A | Y | COB | R | Hal |
|---|---|---|---|---|---|
| 1 | αG | βH | BH | —CH₂COCH₂S—5-TETR—1-Me | Cl |
| 2 | " | " | " | —CH₂COCH₂OAc | " |
| 3 | " | " | " | " | Br |
| 4 | " | " | " | —CH₂CH——CH₂ \\O/ | " |
| 5 | " | " | " | " | Cl |
| 6 | βG | αMeO | " | —CH₂COCH₂S—5-TETR—1-Me | " |
| 7 | " | αH | " | —CH₂COCH₂S—5-TETR | " |
| 8 | " | " | " | —CH₂COCH₂S—5-TETR—2-Me | " |
| 9 | " | " | " | —CH₂COCH₂S—5-TETR—1-isoBu | " |
| 10 | " | " | " | —CH₂COCH₂S—5-TETR—1-Ph | " |
| 11 | " | " | " | —CH₂COCH₂S—5-TETR—1-CH₂COO-t-Bu | " |
| 12 | " | " | " | —CH₂COCH₂S—5-TETR—2-CH₂COO-t-Bu | " |
| 13 | " | " | " | —CH₂COCH₂S—5-TDAZ—2-Me | " |
| 14 | " | " | " | —CH₂COCH₂OMe | " |
| 15 | " | " | " | —CH₂COCH₂OAc | " |
| 16 | " | " | " | —CH₂CH——CH₂ \\O/ | " |
| 17 | " | " | " | —CH₂COCH₂S—5-TETR—1-Me | " |
| 18 | βB | αMeO | BZ | —CH₂COCH₂S—5-TETR—1-Me | " |
| 19 | " | " | " | —CH₂CH——CH₂ \\O/ | Br |
| 20 | αG | βH | BH | —CH₂COCH₂OAc | MeSO₃ |

| Ex. No. | S.M. (g) | CH₂Cl₂ (ml) | SOHal₂ (ml) | Base (ml) | Temp. (°C.) | Time (min.) | Crop (g) |
|---|---|---|---|---|---|---|---|
| 1 | 3.30 | 35 | 0.48 | C₅H₅N (0.45) | 0 | 30 | 3.37 |
| 2 | 7.9 | 80 | 2.5 | C₅H₅N (1.1) | " | 20 | 8.3 |
| 3 | 0.5 | 5 | 0.2 | C₅H₅N (0.21) | " | 25 | 0.54 |

TABLE L-continued
(Halogenation and sulfonylation)

$$\underset{\substack{|\\COB}}{\overset{\substack{Y\\|}}{A\sim}}\!\!\!\!\!\overset{OR}{\underset{CHOH}{\diagdown}} \longrightarrow \underset{\substack{|\\COB}}{\overset{\substack{Y\\|}}{A\sim}}\!\!\!\!\!\overset{OR}{\underset{NCHHal}{\diagdown}}$$

| | | | | | | | |
|---|---|---|---|---|---|---|---|
| 4 | 2.7 | 80 | 1.2 | MeN⌒O (1.65) | " | 30 | 3.0 |
| 5 | 0.3 | 5 | 0.143 | C₅H₅N (0.091) | " | 15 | 0.35* |
| 6 | 0.35 | 3 | 0.073 | C₅H₅N (0.073) | −15 | 10 | 0.35 |
| 7 | 5.16 | 30 | 0.61 | C₅H₅N (0.67) | 0 | 60 | 5.14 |
| 8 | 1.71 | 10 | 0.24 | C₅H₅N (0.22) | " | 20 | 1.66 |
| 9 | 5.30 | 53 | 1.25 | C₅H₅N (0.86) | 0 / rt | 240 / 210 | 5.40 |
| 10 | 8.91 | 30 | 0.49 | C₅H₅N (0.45) | 0 | 20 | 3.92 |
| 11 | 0.69 | 6 | 0.082 | C₅H₅N (0.076) | " | 30 | 0.70 |
| 12 | 1.75 | 30 | 0.21 | C₅H₅N (0.22) | " | 30 | 1.85 |
| 13 | 0.90 | 10 | 0.30 | C₅H₅N (0.11) | " | 120 | 0.90 |
| 14 | 1.81 | 10 | 0.72 | C₅H₅N (0.27) | " | 30 | 1.88 |
| 15 | 0.90 | 10 | 0.34 | C₅H₅N·(0.13) | " | 90 | 0.85 |
| 16 | 1.03 | 5 | 0.43 | C₅H₅N (0.48) | −30 / 0 | 15 / 15 | 1.0 |
| 17 | 3.8 | 35 | 0.66 | C₅H₅N (0.49) | 0 | 45 | 3.9 |
| 18 | 7.25 | 75 | 1.36 | Et₃N (1.34) | 25 | 25 | — |
| 19 | 7.97 | 140 | 2.04 | MeN⌒O (2.89) | 0 | 20 | — |
| 20 | 0.5 | 5 | MeSO₂Cl 0.21 Et₃N (0.36) | | " | 77 | 0.54 |

*Epoxy ring ruptured during the reaction to give a halohydrin.

TABLE M
(Phosphoranilidene introduction)

$$\underset{\substack{|\\COB}}{\overset{\substack{Y\\|}}{A\sim}}\!\!\!\!\!\overset{OR}{\underset{NCHHal}{\diagdown}} \longrightarrow \underset{\substack{|\\COB}}{\overset{\substack{Y\\|}}{A\sim}}\!\!\!\!\!\overset{OR}{\underset{NC=PPh_3}{\diagdown}}$$

| Ex. No. | A | Y | COB | R | Hal | S.M. (g) | CH₂Cl₂ (ml) | Ph₃P (g) | Temp. (°C.) | Time (min.) | Crop (g) |
|---|---|---|---|---|---|---|---|---|---|---|---|
| 1 | αG | βH | BH | —CH₂COCH₂S—5-TETR—1-Me | Cl | 3.37 | 35 | 4.41 | refl | 240 | 2.09 |
| 2 | " | " | " | " | " | 8.3 | 80 | 9.0 | " | 240 | 3.6 |
| 3 | " | " | " | —CH₂COCH₂OAc | " | 0.58 | 6 | 0.79 | " | 240 | 0.257 |
| 4 | " | " | " | —CH₂CH—CH₂ \\ / O | " | 0.34 | 4 | 0.47 | " | 150 | 0.201 |
| 5 | " | " | " | " | Br | 3.0 | 80 | 3.9 | " | 90 | (1.17)* |
| 6 | βG | αMeO | " | —CH₂COCH₂S—5-TETR—1-Me | Cl | 0.35 | 4 | 0.47 | " | 300 | 0.768 |
| 7 | " | αH | " | —CH₂COCH₂S—5-TETR | " | 5.14 | 40 | 5.00 | " | 180 | 1.90 |
| 8 | " | " | " | —CH₂COCH₂S—5-TETR—2-Me | " | 1.66 | 20 | 2.4 | " | 180 | 1.15 |
| 9 | " | " | " | —CH₂COCH₂S—5-TETR—1-isoBu | " | 5.40 | 50 | 5.0 | " | 280 | 2.06 |
| 10 | " | " | " | —CH₂COCH₂S—5-TETR—1-Ph | " | 3.92 | 40 | 2.5 | " | 300 | 4.10 |
| 11 | " | " | " | —CH₂COCH₂S—5-TETR—1-CH₂COOt-Bu | " | 0.70 | 10 | 1.0 | " | 180 | 0.62 |
| 12 | " | " | " | —CH₂COCH₂S—5-TETR—2-CH₂COOt-Bu | " | 1.85 | 20 | 1.6 | " | 240 | 1.20 |
| 13 | " | " | " | —CH₂COCH₂S—5-TDAZ—2-Me | " | 0.90 | 10 | 0.9 | " | 240 | 0.32 |
| 14 | " | " | " | —CH₂COCH₂OMe | " | 1.88 | 10 | 1.0 | " | 240 | 1.77 |
| 15 | " | " | " | —CH₂COCH₂OAc | " | 0.85 | 7 | 0.9 | " | 150 | 0.65 |
| 16 | " | " | " | —CH₂CHOH—CH₂Cl | " | 1.0 | 10 | 1.0 | " | 120 | 0.62 |
| 17 | " | " | " | —CH₂COCH₂S—5-TETR—1-Me | " | 4.95 | 40 | 6.0 | " | 180 | 5.03 |
| 18 | βB | αMeO | BZ | " | " | —** | 75 | 9.97 | " | 180 | 6.52 |

TABLE M-continued
(Phosphoranilidene introduction)

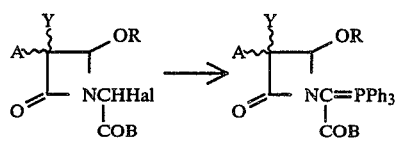

| Ex. No. | A | Y | COB | R | Hal | S.M. (g) | $CH_2Cl_2$ (ml) | $Ph_3P$ (g) | Temp. (°C.) | Time (min.) | Crop (g) |
|---|---|---|---|---|---|---|---|---|---|---|---|
| 19 | " | " | " | —CH$_2$CH—CH$_2$ \\ \\O/ | Br | —** | 140 | 5.05 | rt | 60 | (8.91)* |

*Epoxy ring ruptured during the reaction. The reaction is carried out in the presence of 1.9 ml dimethylanilin.
**Continuous reaction from reaction L, Ex. No. 18 and 19.

TABLE N
(Nucleophile exchange)

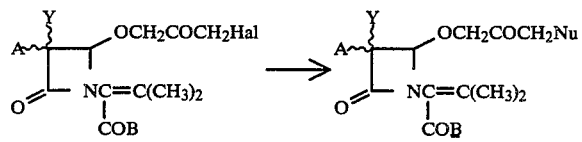

| Ex. No. | A | Y | COB | Hal | Nu | S.M. (g) | HNu (g) | Catalyst (ml) | Solvent (ml) | Temp. (°C.) | Time (min.) | Crop (g) |
|---|---|---|---|---|---|---|---|---|---|---|---|---|
| 1 | αG | βH | BH | Br | —S—5-TETR—1-Me | 0.603 | 0.124 | Et$_3$N(0.13) | An(6) | 0 | 30 | 0.161 |
| 2 | " | " | " | I | " | 0.327 | 0.063 | Et$_3$N(0.075) | An(10) | " | 35 | 0.192 |
| 3 | βG | αMeO | " | Br | " | 0.176 | 0.035 | Et$_3$N(0.038) | An(1.8) | " | 45 | 0.088 |
| 4 | " | αH | BZ | " | " | 0.206 | 0.080 | Na salt | An(4) | rt | 10 | 0.229 |
| 5 | " | " | " | " | —OAc | 3.100 | 0.730 | " | HCONMe$_2$(16) | " | 120 | 3.40 |
| 6 | βB | αMeO | BZ | Br | —S—5-TETR—1-Me | 3.24 | 0.631 | " | HCONMe$_2$(49) | 0 | 70 | 3.382 |
| 7 | βG | αH | BH | Cl | —S—5-TDAZ—2-Me | 0.14 | 26 | Et$_3$N(0.028) | An(1) | " | 30 | 0.049 |

TABLE P
(Cyclization)

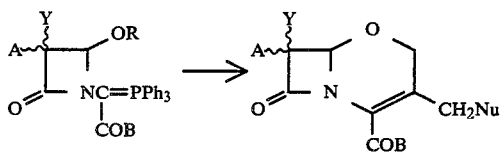

| Ex. No. | A | Y | COB | R | S.M. (g) | Dioxane (ml) | Temp. (°C.) | Time (hr) | Crop (g) |
|---|---|---|---|---|---|---|---|---|---|
| 1 | αG | βH | BH | —CH$_2$COCH$_2$S—5-TETR—1-Me | 2.09 | 20 | refl. | 17 | 0.688 |
| 2 | " | " | " | —CH$_2$COCH$_2$OAc | 3.31 | 70 | " | 20 | 1.79 |
| 3 | βG | αMeO | " | —CH$_2$COCH$_2$S—5-TETR—1-Me | 0.768 | 8 | " | 5.5 | 0.151 |
| 4 | " | αH | " | —CH$_2$COCH$_2$S—5-TETR | 1.90 | 20 | " | 15 | 0.33 |
| 5 | " | " | " | —CH$_2$COCH$_2$S—5-TETR—2-Me | 1.12 | 18 | " | 18 | 0.56 |
| 6 | " | " | " | —CH$_2$COCH$_2$S—5-TETR—isoBu | 1.31 | 36 | " | 15 | 0.70 |
| 7 | " | " | " | —CH$_2$COCH$_2$S—5-TETR—1-Ph | 4.10 | 40 | " | 15 | 2.31 |
| 8 | " | " | " | —CH$_2$COCH$_2$S—5-TETR—1-CH$_2$COOt-Bu | 0.62 | 10 | " | 18 | 0.30 |
| 9 | " | " | " | —CH$_2$COCH$_2$S—5-TETR—2-CH$_2$COOt-Bu | 1.20 | 30 | " | 20 | 0.47 |
| 10 | " | " | " | —CH$_2$COCH$_2$S—5-TDAZ—2-Me | 0.32 | 5 | " | 18 | 0.14 |
| 11 | " | " | " | —CH$_2$COCH$_2$OMe | 1.77 | 20 | " | 40 | 0.87 |
| 12 | " | " | " | —CH$_2$COCH$_2$OAc | 0.63 | 9 | " | 20 | 0.40 |
| 13 | " | " | " | —CH$_2$COCH$_2$S—5-TETR—1-Me | 5.03 | 50 | " | 15.5 | 2.27 |
| 14 | βB | αMeO | BZ | " | 9.00 | — | " | 2.5 | 3.44 |

TABLE Q
(Deacylation)

$$\text{Acyl-NH} \overset{Y}{\underset{O}{\bigg\rvert}} \overset{}{\underset{N}{\bigg\rvert}} \overset{CH_2Nu}{\underset{COB}{\bigg\rvert}} \longrightarrow H_2N \overset{Y}{\underset{O}{\bigg\rvert}} \overset{}{\underset{N}{\bigg\rvert}} \overset{CH_2Nu}{\underset{COB}{\bigg\rvert}}$$

| Ex. No. | A | Y | COB | Nu | S.M. (g) | CH₂Cl₂ (ml) | PCl₅ (g) | C₅H₅N (ml) | Temp. (°C.) | Time (min.) | CH₃OH (ml) | Temp. (°C.) | Time (min.) | H₂O (ml) | Time (min.) | Crop (g) |
|---|---|---|---|---|---|---|---|---|---|---|---|---|---|---|---|---|
| 1 | αG | βH | BH | —S—5-TETR—1-Me | 0.50 | 12 | 0.394 | 0.136 | −20 | 30 | 6 | rt | 60 | 2.67 | — | 0.333 |
| 2 | " | " | " | —OAc | 1.224 | 50 | 1.26 | 0.55 | rt / −20 | 25 / 20 | 10 | 0 | 30 | — | — | 0.772* |
| 3 | βG | αMeO | " | —S—5-TETR—1-Me | 0.101 | 2 | 0.085 | 0.05 | 0 / −20 | 140 / 90 | 2 | rt | 25 / 30 | — | — | 0.013 |
| 4 | " | αH | " | —S—5-TETR | — | — | — | — | — | — | — | — | — | — | — | — |
| 5 | " | " | " | —S—5-TETR—2-Me | 0.564 | 10 | 0.393 | 0.15 | −20 | 30 | 3 | rt | 30 | 2.0 | 10 | 0.207 |
| 6 | " | " | " | —S—5-TETR—1-isoBu | 0.589 | — | 0.393 | 0.15 | rt / −20 | 30 / 90 | 4 | " | 30 | 2.0 | 30 | 0.205 |
| 7 | " | " | " | —S—5-TETR—1-Ph | 1.575 | 25 | 0.996 | 0.385 | rt / −20 | 30 / 30 | 10 | " | 30 | 5.0 | 30 | 1.228 |
| 8 | " | " | " | —S—5-TETR—1-CH₂COO—t-Bu | 0.300 | 10 | 0.180 | 0.07 | −20 / rt | 30 / 30 | 4 | " | 30 | 2.0 | 30 | 0.189 |
| 9 | " | " | " | —S—5-TETR—2-CH₂COO—t-Bu | 0.470 | 10 | 0.282 | 0.11 | −20 / rt | 30 / 40 | 10 | " | 30 | 4.0 | 30 | 0.470 |
| 10 | " | " | " | —S—5-TDAZ—2-Me | 0.382 | 8 | 0.259 | 0.10 | 20 / −20 | 30 / 30 | 8 | " | 30 | 4.0 | 30 | 0.274 |
| 11 | " | " | " | —OMe | 0.705 | 10 | 0.573 | 0.22 | rt / 0 | 30 / 10 | 10 | " | 30 | 5.0 | 30 | 0.416 |
| 12 | " | " | " | —OAc | 0.265 | 10** | 0.180 | 0.09 | rt / 0 | 60 / 30 | 5 | " | 20 | 10.0 | 20 | 0.250 |
| 13 | " | " | " | —S—5-TETR—1-Me | 0.955 | 24 | 0.666 | 0.26 | rt / −20 | 30 / 90 | 12 | " | 30 | 6.0 | 30 | 0.661 |
| 14 | βB | αMeO | BZ | " | 1.07 | 5 | 0.834 | 0.49 | rt / 25 | 30 / 90 | 11 | 10 | 150 | — | — | 0.365 |

*isolated as toluene-p-sulfonate.
**Benzene was used in place of methylene chloride as solvent for the reaction.

TABLE R
(Methoxylation)

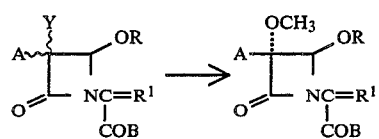

| Ex. No. | A | Y | COB | R | $R^1$ | S.M. (g) | $CH_2Cl_2$ (ml) | t-BuOCl (ml) | $LiOCH_3$/MeOH (ml) | Temp. (°C.) | Time (hr) | Crop (g) |
|---|---|---|---|---|---|---|---|---|---|---|---|---|
| 1 | αG | βH | BH | —CH₂C≡CH | =CMe₂ | 0.139 | 2.7 | 0.048 | 2M(—) | −40 | 40 | 0.144 |
| 2 | " | " | " | —CH₂CH≡CH | " | 0.265 | 5 | 0.07 | 2M | −30 | 15 | 0.185 |
| 3 | " | " | " | —CH₂CH—CH₂ (epoxide) | " | 1.679 | 30 | 0.56 | 2M(1.87) | −30 | 20 | 1.796 |
| 4 | " | " | " | —CH₂C≡CBr | " | 7.44 | 74 | 1.7 | 2M(7.42) | — | 10 | 6.70 |
| 5 | " | " | " | " | " | 0.273 | THF(60) | 0.06 | 2M(0.88) | −80∼−50 | 1/6 | 0.195 |

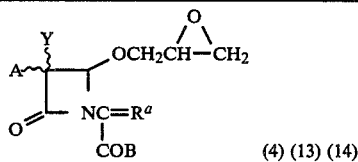

(4) (13) (14)

| A | Y | COB | =$R^a$ | IR: $\nu_{max}^{CHCl_3}$ (cm$^{-1}$) |
|---|---|---|---|---|
| βG— | αH— | BH | =C(CH₃)₂ | 3433,1778,1724,1680,1632,1506. |
| βCbz | " | " | " | 3445,1778,1724,1632,1508. |
| αG— | βH— | " | " | 3410,1775,1720,1680. |
| " | " | " | =O | 3425,1824,1752,1710,1680. |
| " | " | " | ⟨OH, H⟩ | 3600–3200,1780,1750,1670. |
| " | " | " | ⟨Br, H⟩ | 3425,1795,1754,1682,1185,1130. |
| βG— | αMeO | " | =C(CH₃)₂ | NMR: $\delta^{CDCl_3}$ 2.07s3H,2.22s3H,2.2–3.3m3H, 3.45brs3H,4.23s2H,6.06brs1H,6.80brs1H, 6.98s1H,7.34m15H. |
| βB— | αMeO | BZ | " | 1780,1725,1690. |
| αB— | βH— | " | " | 1775,1720,1665. |
| " | " | " | ⟨OH, H⟩ | 1780,1750,1685. |

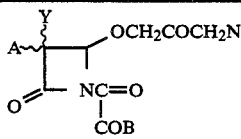

(9) (13)

| A | Y | COB | Nu | IR: $\nu_{max}^{CHCl_3}$ |
|---|---|---|---|---|
| αG— | βH— | BH | —S—5-TETR—1-Me | 3400,1823,1748,1708. |
| " | " | " | —OAc | 3430,1830,1740,1710,1680. |
| βG— | αMeO | " | —S—5-TETR—1-Me | |
| " | αH | " | —S—5-TETR | 3415,1930,1750,1718,1695. |
| " | " | " | —S—5-TETR—2-Me | |
| " | " | " | —S—5-TETR—1-isoBu | 3413,1823,1745,1708,1687,1602. |
| " | " | " | —S—5-TETR—1-Ph | 3425,1830,1750,1714,1690. |
| " | " | " | —S—5-TETR—1-CH₂BH | 1830,1755,1710,1690sh. |
| " | " | " | —S—5-TETR—1-CH₂COOtBu | 3420,1830,1755,1715,1690. |
| " | " | " | —S—5-TETR—2-CH₂COOtBu | 3430,1830,1755,1715,1690. |
| " | " | " | —S—5-TDAZ—2-Me | 3440,1832,1755,1715,1690. |
| " | " | " | —OMe | 3430,1830,1750,1715,1690. |
| " | " | " | —OAc | 3430,1830,1750,1715. |
| " | " | " | (4-subst.=OCH₂CH—CH₂ epoxide) | 3425,1824,1752,1710,1682. |

TABLE R-continued

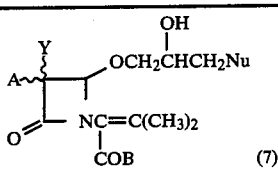
(7)

| A | Y | COB | Nu | IR: $\nu_{max}^{CHCl_3}$ |
|---|---|---|---|---|
| αG— | βH— | BH | —Cl | 3400,1775,1720,1680. |
| " | " | " | —Br | 3400,1760,1720,1670. |
| " | " | " | —S—5-TETR—1-Me | |
| " | " | " | —OAc | NMR: 2.00s3H,2.05s3H,2.25s3H. |
| βG— | αMeO | " | —Br | 3600–3200,1775,1720,1690,1060. |
| " | " | " | —S—5-TETR—1-Me | NMR: 1.98s3H,2.28s3H,3.47s3H, 3.86s3H. |
| " | αH— | " | —S—5-TETR | 3425,3300,1781,1734,1672. |
| " | " | " | —S—5-TETR—2-Me | |
| " | " | " | —S—5-TETR—isoBu | 3423,1773,1722,1677. |
| " | " | " | —S—5-TETR—1-Ph | 3425,3350,1777,1727,1678. |
| " | " | " | —S—5-TETR—1-CH$_2$COOH | 1780,1735,1710sh,1670. |
| " | " | " | —S—5-TDAZ—2-Me | 3425,3320,1774,1722,1675. |
| " | " | " | —OMe | 3425,3320,1774,1722,1675. |
| " | " | " | —OAc | 3425,1780,1730,1680. |
| " | " | " | —Cl | 3440,1780,1727,1682. |
| " | " | " | —OH | 3420,1774,1720,1670,1504. |
| " | " | " | —OH | 3600,3445,1778,1725,1632,1508. |
| βB | αMeO | BZ | —S—5-TETR—1-Me | 3430,1775,1725,1680. |
| " | " | " | —Br | NMR: $\delta^{CDCl_3}$ 2.03s3H,2.25s3H, 3.0–4.0m6H,4.93d(6Hz)1H, 5.20s2H,7.2–7.9m11H. |

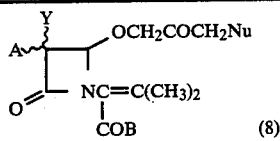
(8)

| A | Y | COB | Nu | IR: $\nu_{max}^{CHCl_3}$ (cm$^{-1}$) |
|---|---|---|---|---|
| αG— | βH— | BH | —Cl | 3410,1780,1725,1680. |
| " | " | " | —Br | 3400,1770,1720,1675. |
| " | " | " | —S—5-TETR—1-Me | — |
| " | " | " | —OAc | — |
| " | " | " | —Br | 1771,1750,1720,1680,1601,1181. |
| βG— | αMeO | " | —S—5-TETR—1-Me | 3410,1778,1720,1695. |
| " | αH— | " | —S—5-TETR | 3425,1780,1730,1680. |
| " | " | " | —S—5-TETR—2-Me | — |
| " | " | " | —S—5-TETR—1-isoBu | 3423,1777,1726,1680. |
| " | " | " | —S—5-TETR—1-Ph | 3430,1792,1730,1680. |
| " | " | " | —S—5-TETR—1-CH$_2$BH | 1780,1725,1685. |
| " | " | " | —S—5-TETR—1-CH$_2$COOtBu | 1783,1755,1690. |
| " | " | " | —S—5-TETR—2-CH$_2$COOtBu | 1782,1760,1730,1690. |
| " | " | " | —S—5-TDAZ—2-Me | 3430,1779,1725,1680. |
| " | " | " | —OMe | NMR: 1.97s3H,2.23s3H,3.28s3H. |
| " | " | " | —OAc | 3440,1780,1740. |
| " | " | " | —Cl | 3430,1780,1722,1680. |
| " | " | BZ | —OAc | 3430,1780,1745,1725,1690, 1640,1500. |
| " | " | " | —S—5-TETR—1-Me | 3420,1780,1725,1680. |
| βB | αMeO | BZ | " | 1775,1730,1680. |

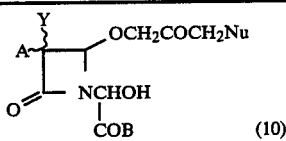
(10)

| A | Y | COB | Nu | IR: $\nu_{max}^{CHCl_3}$ (cm$^{-1}$) |
|---|---|---|---|---|
| αG | βH | BH | —S—5-TETR—1-Me | 3550,3200,1786,1750,1678,1100. |
| " | " | " | —OAc | 3420,1790,1745,1680. |
| βG | αMeO | " | —S—5-TETR—1-Me | 3600–3200,1790,1750,1696, 1490,1140. |
| " | αH | " | —S—5-TETR | 3325,1794,1750,1680. |
| " | " | " | —S—5-TETR—2-Me | 3400,3360,1785,1750,1680,1605. |
| " | " | " | —S—5-TETR—1-isoBu | 3411,3320,1784,1743,1678. |
| " | " | " | —S—5-TETR—1-Ph | 3425,3330,1790,1748,1680. |
| " | " | " | —S—5-TETR—1-CH$_2$COOt-Bu | 1795,1758,1685. |
| " | " | " | —S—5-TETR—2-CH$_2$COOt-Bu | 3410,1783,1754,1680. |
| " | " | " | —S—5-TDAZ—2-Me | 3400–3300,1790,1745,1678. |

TABLE R-continued

| | | | | | |
|---|---|---|---|---|---|
| " | " | " | —OMe | | 3425,3350,1790,1746,1680. |
| | | | —OAc | | 3430,1790,1745,1680. |
| | | | | α-epimer | a NMR: $\delta^{CDCl_3}$ 4.05d(4Hz)2H, |
| | | | | | b NMR: $\delta^{CDCl_3}$ 3.87s2H. |
| βB | αMeO | BZ | —S—5-TETR—1-Me | | 1785,1745,1680. |

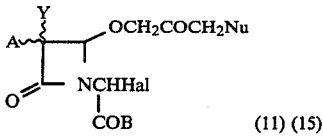

(11) (15)

| A | Y | COB | Nu | Hal | IR: $\nu_{max}^{CHCl_3}$ (cm$^{-1}$) |
|---|---|---|---|---|---|
| αG— | βH— | BH | —S—5-TETR—1-Me | Cl | 3420,1800,1760,1680. |
| " | " | " | —OAc | " | 3420,1790,1740,1675. |
| " | " | " | " | Br | 3420,1795,1745,1780. |
| " | " | " | (4-subst.—OCH$_2$CH—CH$_2$ epoxide) | " | 3425,1795,1754,1682,1185,1130. |
| " | " | " | " | MsO | 3420,1795,1750,1680,1375,1175. |
| βG— | αMeO | " | —S—5-TETR—1-Me | Cl | 1800,1760,1695,1495,1170. |
| " | αH— | " | —S—TETR | " | 1800,1757,1680. |
| " | " | " | —S—5-TETR—2-Me | " | |
| " | " | " | —S—5-TETR—1-isoBu | " | 3386,1792,1752,1670. |
| " | " | " | —S—5-TETR—1-Ph | " | 3430,1800,1754,1682. |
| " | " | " | —S—5-TETR—1-CH$_2$COO-t-Bu | " | |
| " | " | " | —S—5-TETR—2-CH$_2$COO-t-Bu | " | |
| " | " | " | —S—5-TDAZ—2-Me | " | 3420,1792,1750,1678. |
| " | " | " | —OMe | " | 3425,1795,1750,1680. |
| " | " | " | —OAc | " | |
| " | " | " | (4-subst.—OCH$_2$CHCH$_2$Cl, OH) | " | 3425,1790,1752,1676. |

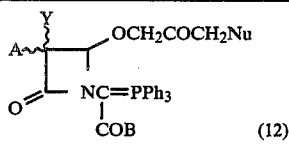

(12)

| A | Y | COB | Nu | IR: $\nu_{max}^{CHCl_3}$ (cm$^{-1}$) |
|---|---|---|---|---|
| αG | βH | BH | —S—5-TETR—1-Me | — |
| " | " | " | —OAc | 3410,1765,1745,1675. |
| βG | αMeO | " | —S—5-TETR—1-Me | — |
| " | αH | " | —S—5-TETR— | 1780,1680,1610. |
| " | " | " | —S—5-TETR—2-Me | — |
| " | " | " | —S—5-TETR—1-isoBu | 3410,1772,1670,1626. |
| " | " | " | —S—5-TETR—1-Ph | 3430,1780,1745,1680,1634. |
| " | " | " | —S—5-TETR—1-CH$_2$COOt-Bu | 3430,1780,1758,1680. |
| " | " | " | —S—5-TETR—2-CH$_2$COOt-Bu | — |
| " | " | " | —S—5-TDAZ—2-Me | 3420,1770,1740,1672,1628. |
| " | " | " | —OMe | 3425,1770,1736,1672,1628. |
| " | " | " | —OAc | 3420,1770,1750,1670. |
| " | " | " | —Cl | 1772,1740,1678,1628. |
| βB | αMeO | BZ | —S—5-TETR—1-Me | 3430,1770,1740,1680,1630,1625. |
| αG | βH | BH | 4-substituent = —OCH$_2$CHCH$_2$Cl, OH | 3425,1778,1680,1632,1118. |
| βG | αH | " | " | 3385,1768,1667,1628. |

TABLE R-continued

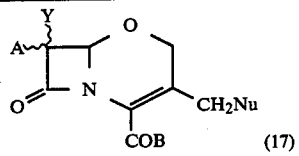

| A | Y | COB | Nu | IR: $\nu_{max}^{CHCl_3}$ (cm$^{-1}$) |
|---|---|---|---|---|
| αG— | βH— | BH | —S—5-TETR—1-Me | 3400,1790,1718,1685. |
| " | " | " | —OAc | 3420,1790,1740,1685. |
| βG— | αMeO | " | —S—5-TETR—1-Me | 3400,1780,1710,1690. |
| " | αH | " | —S—5-TETR | 3420,1800,1722,1680. |
| " | " | " | —S—5-TETR—2-Me | NMR: 3.58s2H,3.66s2H,4.10s3H. |
| " | " | " | —S—5-TETR—1-isoBu | 3420,1800,1715,1683,1635. |
| " | " | " | —S—5-TETR—1-Ph | 3425,1797,1717,1685. |
| " | " | " | —S—5-TETR—1-CH$_2$COOtBu | 3425,1800,1750,1722,1680. |
| " | " | " | —S—5-TETR—2-CH$_2$COOtBu | 3420,1796,1725,1682. |
| " | " | " | —S—5-TDAZ—2-Me | 3430,1798,1720,1680. |
| " | " | " | —OMe | 3430,1798,1723,1680. |
| " | " | " | —OAc | 3440,1800,1740,1680. |
| βB | αMeO | BZ | —S—5-TETR—1-Me | 3440,1789,1723,1691,1640, 1603,1584, mp. 85° C. |

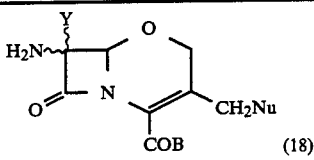

| H$_2$N | Y | COB | Nu | IR: $\nu_{max}^{CHCl_3}$ (cm$^{-1}$) |
|---|---|---|---|---|
| α | βH— | BH | —S—5-TETR—1-Me | 3380,1785,1720. |
| " | " | " | —OAc | 3400,1800,1735,1630. |
| β | αMeO | " | —S—5-TETR—1-Me | 3400,3300,1785,1720,1625,1600. |
| " | " | " | —OAc | 1785,1735,1680,1640. |
| " | αH | " | —S—5-TETR | — |
| " | " | " | —S—5-TETR—2-Me | NMR: 1.74brs2H,4.17s3H,4.60s2H. |
| " | " | " | —S—5-TETR—1-isoBu | 3562,3412,1789,1715,1630. |
| " | " | " | —S—5-TETR—1-Ph | 3425,3355,1793,1722. |
| " | " | " | —S—5-TETR—1-CH$_2$COOtBu | 1795,1753,1722. |
| " | " | " | —S—5-TETR—2-CH$_2$COOtBu | 1793,1758,1733,1633. |
| " | " | " | —S—5-TDAZ—2-Me | 3420,3350,1794,1723. |
| " | " | " | —OMe | 3420,3350,1785,1722. |
| " | " | " | —OAc | — |
| " | αMeO | BZ | —S—5-TETR—1-Me | NMR: $\delta^{CDCl_3}$2.20brs2H,3.45s3H, 3.83s3H,4.27s2H,4.63brs2H, 5.30s2H,7.23–7.50m5H,4.83s1H. |

S. USE OF COMPOUNDS (18)

The Compounds (18) can be acylated in accordance with a conventional acylation, if required followed by deprotection of attached protective group of 4-carboxy to give antibacterial Compounds (17). Acylation can be effected by the action of a reactive derivative (e.g. free acid in the presence of condensing reagent (e.g. dicyclohexylcarbodiimide, or 2-ethoxy-1-ethoxycarbonyl-1,2-dihydroquinoline), halide in the presence of acid acceptor (e.g. pyridine, quinoline, triethylamine, or N-methylmorpholine), reactive ester or amide) of acids having the desired acyl group, in an inert solvent (e.g. methylene chloride, chloroform, acetone, ethyl acetate, or water) at generally —° C. to 40° C. for 15 minutes to 12 hours. Usually 1 to 1.5 mole equivalents of acylating reagent is used to acylate Compound (18).

Said deprotection of attached protective group of 4-carboxy can be effected by the action of acid, base, hydrogen, or like conventional methods well known to those skilled in the art. The acids include mineral acid, strong organic acid like trifluoroacetic acid, and base being e.g. hydroxide or carbonate of alkali metal alkali metal thiophenoxide, etc.

EXAMPLE S

To a solution of diphenylmethyl 7β-amino-3-(2-methyltetrazol-5-yl)thiomethyl-1-oxadethia-3-cephem-4-carboxylate (105 mg) and α-phenylmalonic acid monobenzhydryl ester (277 mg) in tetrahydrofuran (2 ml) is added N-ethoxycarbonyl-2-ethoxy-1,2-dihydroquinoline (163 mg) in five portions, and the mixture is stirred at room temperature for 5 hours. The reaction mixture is diluted with ethyl acetate, washed with 1N-hydrochloric acid, 5% aqueous solution of sodium hydrogencarbonate, and water, and dried over magnesium sulfate. The residue obtained by evaporating the solution is chromatographed over silica gel containing 10% water (10 g) to give diphenylmethyl 7β-(α-phenyl-α-diphenylmethoxycarbonylacetamido)-3-(2-methyltetrazol-5-yl)thiomethyl-1-oxadethia-3-cephem-4-carboxylate (126 mg) as colorless foam from the fraction eluted with a mixture of ethyl acetate and acetic acid (5:1). Yield: 71.2%.

IR: $\nu_{max}^{CHCl_3}$ 3366, 3280, 1797, 1720, 1680 cm$^{-1}$.

NMR: $\delta^{CDCl_3}$ 4.17s3H, ca. 4.2m2H, 4.53s2H, 4.71s0.5H, 4.72s0.5H, 5.02d(4 Hz), 1H5.70dd(10;4 Hz)1H, 6.92s1H, 6.95s1H, 7.2–8.0m20H.

(2) To a solution of diphenylmethyl 7β-(α-phenyl-α-diphenylmethoxycarbonylacetamido)-3-(2-methyltetrazol-5-yl)thiomethyl-1-oxadethia-3-cephem-4-carboxylate (126 mg) are added anisole (0.8 ml) and trifluoroacetic acid (0.8 ml) under nitrogen atmosphere, and the mixture is stirred for 3 hours at 0° C. The residue obtained by evaporation of the reaction mixture is dissolved in ethyl acetate, and purified by chromatography over silica gel containing 10% water (3 g) to give 7β-(α-phenyl-α-carboxyacetamido)-3-(2-methyltetrazol-5-yl)thiomethyl-1-oxadethia-3-cephem-4-carboxylic acid (32 mg) from the fraction eluted with a mixture of ethyl acetate and acetic acid (9:1). Colorless powder. Yield: 43.2%.

IR: $\nu_{max}^{KBr}$ 3400, 2920, 2500, 1775, 1660 cm$^{-1}$.

Some of the products made as above from Compounds (18) are listed in Table S with IR spectra. They are active against gram positive and negative bacteria and useful for treating human and veterinary bacterial infection at a daily dose of 0.1 g to 5 g preferably intravenus administration of sodium salts in aqueous solution.

TABLE S

Physical Constants of [structure with A, Y, O, N, COOH, CH₂Nu]

| A | Y | Nu | m.p. | IR: $\nu_{max}^{KBr}$ (cm$^{-1}$) |
|---|---|---|---|---|
| PhCHCONH— <br> \| <br> COOH | αH | —S—5-TETR—1-Me | 157–159° | 3420, 2520, 1775, 1674, 1606, 1529, 1376. |
| PhCHCONH— <br> \| <br> COOH | " | —S—5-TDAZ—2-Me | 130–132° | 3410, 1772, 1600. |
| PhCHCONH— <br> \| <br> OH | " | " | 170° | 1778, 1710, 1675. |
| PhCH₂CONH— | " | " | 107–115° | 3430, 1799, 1720, 1685. |
| PhCH₂CONH— | " | —OMe | 108–115° | 3400, 1778, 1675. |
| PhCHCONH— <br> \| <br> NH₂ | " | " | 145° | 3410, 3060, 1781, 1685. |
| PhCHCONH— <br> \| <br> COOH | " | " | 175–195° | 1767, 1682, 1605. |
| PhCH₂CONH— | " | —OAc | 191–193° | 3280, 1790, 1760, 1715. |
| [thiophene]-CH₂CONH— | " | " | 181–183° | 3380, 1790, 1760, 1715, 1665. |
| PhCHCONH— <br> \| <br> OH | " | " | — | 3370, 1785, 1740, 1720, 1675. |
| PhCHCONH— <br> \| <br> COOH | " | " | — | 3300, 1780, 1720, 1680. |
| PhCHCONH— <br> \| <br> COOH | " | —S—5-TETR—1-Ph | 145–147° | 1777, 1668, 1597. |
| [thiophene]-CH—CONH— <br> \| <br> COOH | " | —S—5-TETR—1-isoBu | — | 3400, 1785, 1680. |
| PhCHCONH— <br> \| <br> COOH | " | —S—5-TETR—1-isoBu | — | 3385, 2680–2525, 1780, 1715, 1665. |
| [thiophene]-CHCONH— <br> \| <br> COOH | " | —S—5-TETR—2-CH₂COOH | — | 1783, 1732, 1668. |

TABLE S-continued

Physical Constants of $$\text{structure with } Y, A, O, N, CH_2Nu, COOH$$

| A | Y | Nu | m.p. | IR: $\nu_{max}^{KBr}$ (cm$^{-1}$) |
|---|---|---|---|---|
| PhCHCONH—<br>\|<br>COOH | " | " | — | 1790, 1730, 1635. |
| 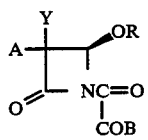CHCONH—<br>\|<br>COOH | " | —S—5-TETR—2-Me | — | 1783, 1712, 1670. |
| PhCHCONH—<br>\|<br>COOH | " | " | — | 3400, 2920, 2500, 1775, 1660. |
| PhCHCONH—<br>\|<br>COOCH$_2$C$_6$H$_4$NO$_2$ | αMeO | —OAc | — | — |
| α-PhCH$_2$CONH— | βH | —OAc | — | 3520, 1780, 1740, 1650. |
| HO—⟨⟩—CHCONH—<br>\|<br>COOH | αH | —S—5-TETR—1-Me | 130–142° | 3400, 1787, 1740, 1650. |
| ⟨S⟩—CHCONH—<br>\|<br>COOH | " | " | 156–160° | 3390, 1765, 1670, 1608, 1520. |
| PhCHCONH—<br>\|<br>COOH | αMeO | " | 110–116° | 1780, 1717, 1631. |
| HO—⟨⟩—CHCONH—<br>\|<br>COOH | " | " | 117–122° | 1780, 1719, 1632. |
| HO—⟨⟩—CHCONH—<br>\|<br>COO—5-indanyl | " | " | 123–126° | 3385, 1785, 1727, 1705, 1631, 1613, 1595. |
| ⟨S⟩—CHCONH—<br>\|<br>COOH | " | " | 110–114° | 1780, 1705. |

What is claimed is:
1. A compound of the formula

$$\begin{array}{c} Y \quad OR \\ A \diagdown \diagup \\ \square \\ O \diagup \diagdown N{-}C{=}O \\ \quad\quad\quad | \\ \quad\quad\quad COB \end{array}$$

wherein
A is amino or acylamino selected from
(1) phenylacetamido,
(2) phenoxyacetamido,
(3) benzamido,
(4) thienylacetamido,
(5) α-hydroxy- or (C$_1$ to C$_5$)alkanoyloxy-α-phenylacetamido,
(6) N-t-butoxycarbonyl-α-phenylglycinamido,
(7) α-phenylmalonamido,
(8) N-(4-ethyl-2,3-dioxopiperazin-1-yl)carbonyl-α-phenylglycinamdio,
(9) (C$_1$ to C$_5$)alkoxycarbonylamino,
(10) cyclohexyloxycarbonylamino,
(11) cyclopropylmethoxycarbonylamino, and
(12) methanesulfonylethoxycarbonylamino, COB is carboxy or protected carboxy selected from those forming
- (C₁ to C₅)alkyl esters,
- (C₂ to C₁₀)alkanoylalkyl esters,
- (C₁ to C₅)haloalkyl esters,
- (C₂ to C₁₀)alkoxyalkyl esters,
- (C₁ to C₁₀)aminoalkyl esters,
- monocyclic aryl esters,
- mono- or bicyclic aralkyl esters,
- N,N'-diisobutylhydrazide,
- alkali metal salts,
- alkaline earth metal salts, and
- (C₁ to C₆)alkylamine salts;

R is a group represented by the formula:

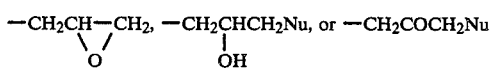

wherein Nu is a nucleophilic group selected from hydroxy, (C₁ to C₅)alkoxy, (C₁ to C₅)alkylthio, (C₁ to C₅)alkanoyloxy, (C₁ to C₅)alkanoylthio, monocyclic arylthio, monocyclic aralkylthio, tetrazolylthio, (C₁ to C₅)alkyltetrazolylthio, (C₁ to C₅)alkoxycarbonylmethyltetrazolylthio, thiadiazolylthio, (C₁ to C₅)alkylthiadiazolylthio and triazolylthio
and
Y is hydrogen or methoxy.

2. A compound claimed in claim 1, that is a compound of the formula

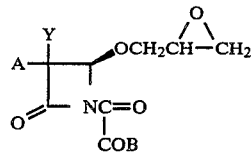

wherein A, Y and COB are as defined in claim 1.

3. A compound claimed in claim 1, that is a compound of the formula

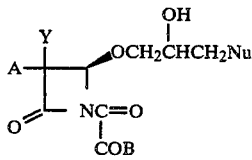

wherein A, Y, Nu and COB are as defined in claim 1.

4. A compound claimed in claim 1, that is a compound of the formula wherein A, Y, Nu and COB are as defined in claim 1.

5. A compound claimed in claim 1, wherein COB is benzyl or diphenylmethyl ester.

6. A compound claimed in claim 1, wherein Y is 3α-methoxy.

7. A compound claimed in claim 1 wherein Y is 3β-hydrogen.

* * * * *